(12) United States Patent
Scott et al.

(10) Patent No.: US 10,842,499 B2
(45) Date of Patent: Nov. 24, 2020

(54) SURGICAL CLIP APPLIER WITH WIDE APERTURE SURGICAL CLIPS

(71) Applicant: Ethicon LLC, Guaynabo, PR (US)

(72) Inventors: Gregory Scott, Cincinnati, OH (US); Michael J. Stokes, Cincinnati, OH (US); Disha Labhasetwar, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 184 days.

(21) Appl. No.: 15/891,609

(22) Filed: Feb. 8, 2018

(65) Prior Publication Data

US 2019/0239892 A1    Aug. 8, 2019

(51) Int. Cl.
| | | |
|---|---|---|
| *A61B 17/12* | (2006.01) | |
| *A61B 17/128* | (2006.01) | |
| *A61B 17/122* | (2006.01) | |
| *A61B 34/00* | (2016.01) | |
| *A61B 34/37* | (2016.01) | |
| *A61B 17/29* | (2006.01) | |
| *A61B 17/10* | (2006.01) | |
| *A61B 34/30* | (2016.01) | |
| *A61B 17/00* | (2006.01) | |

(52) U.S. Cl.
CPC ........ *A61B 17/1285* (2013.01); *A61B 17/122* (2013.01); *A61B 34/25* (2016.02); *A61B 34/37* (2016.02); *A61B 17/10* (2013.01); *A61B 34/70* (2016.02); *A61B 2017/00477* (2013.01); *A61B 2017/2939* (2013.01); *A61B 2034/305* (2016.02)

(58) Field of Classification Search
CPC ... A61B 17/10; A61B 17/068; A61B 17/0682; A61B 17/00684
See application file for complete search history.

(56) References Cited

U.S. PATENT DOCUMENTS

| | | | | |
|---|---|---|---|---|
| 4,391,401 A | * | 7/1983 | Moshofsky | ........ A61B 17/0684 227/19 |
| 4,430,997 A | | 2/1984 | DiGiovanni et al. | |
| 4,512,345 A | * | 4/1985 | Green | .................. A61B 17/128 606/143 |

(Continued)

FOREIGN PATENT DOCUMENTS

EP    0106748 A1    4/1984

OTHER PUBLICATIONS

ISR/WO from PCT/IB2019/050350 (claiming priority to the present application) dated May 27, 2019.

*Primary Examiner* — Alexander J Orkin
(74) *Attorney, Agent, or Firm* — Vorys, Sater, Seymour and Pease LLP

(57) ABSTRACT

An end effector for a surgical clip applier includes an elongate body and a clip track provided within the body and containing one or more surgical clips. Each surgical clip includes a crown and a pair of legs extending longitudinally from the crown and diverging from each other at a diverging opening angle. A pre-forming region is provided within the body and arranged to receive and deform the one or more surgical clips from a first state, where the pair of legs diverge at the diverging opening angle, and a second state, where the diverging opening angle is minimized. First and second jaw members are positioned at a distal end of the body and arranged to receive the one or more surgical clips from the pre-forming region in the second state.

15 Claims, 14 Drawing Sheets

(56) References Cited

U.S. PATENT DOCUMENTS

| | | | | |
|---|---|---|---|---|
| 4,557,263 | A | * 12/1985 | Green | A61B 17/128 |
| | | | | 206/339 |
| 5,456,400 | A | * 10/1995 | Shichman | A61B 17/064 |
| | | | | 227/176.1 |
| 5,626,587 | A | * 5/1997 | Bishop | A61B 17/0682 |
| | | | | 227/175.1 |
| 8,403,945 | B2 | 3/2013 | Whitfield et al. | |
| 8,585,718 | B2 | * 11/2013 | Disch | A61B 17/1285 |
| | | | | 606/143 |
| 9,232,979 | B2 | 1/2016 | Parihar et al. | |
| 2004/0097971 | A1 | * 5/2004 | Hughett | A61B 17/068 |
| | | | | 606/142 |
| 2011/0224696 | A1 | 9/2011 | Huitema et al. | |
| 2016/0287252 | A1 | 10/2016 | Parihar | |
| 2017/0086824 | A1 | * 3/2017 | Khan | A61B 17/1227 |

\* cited by examiner

SURGICAL CLIP APPLIER WITH WIDE APERTURE SURGICAL CLIPS

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical clip appliers having an end effector that stores wide angle surgical clips and transitions the wide angle surgical clips to tissue-ready surgical clips ready for crimping between opposed jaw members.

Embodiments discussed herein describe improvements to clip applier end effectors. The end effectors described herein include an elongate body and a clip track provided within the body and containing one or more surgical clips. Each surgical clip includes a crown and a pair of legs extending longitudinally from the crown and diverging from each other at a diverging opening angle. A pre-forming region is provided within the body and arranged to receive and deform the one or more surgical clips from a first state, where the pair of legs diverge at the diverging opening angle, and a second state, where the diverging opening angle is minimized. First and second jaw members are positioned at a distal end of the body and arranged to receive the one or more surgical clips from the pre-forming region in the second state. Storing the surgical clips in the clip track in the first state allows the surgical clips to be arranged in a nested relationship, which decreases the overall length of the end-effector. The pre-forming region is used to transition the surgical clips into the second state or a "tissue-ready" state capable of being received between the jaw members and crimped over tissue as desired.

In contrast to conventional clip appliers, the surgical clips may be received by the jaw members crown first, which helps mitigate catching the surgical clips on any sharp corners that might obstruct their distal advancement. Moreover, the presently described jaw members may comprise independent or separate plate-like structures that may prove advantageous in facilitating parallel closure of the jaw members, which can reduce the force required to crimp a surgical clip.

Figure 1:
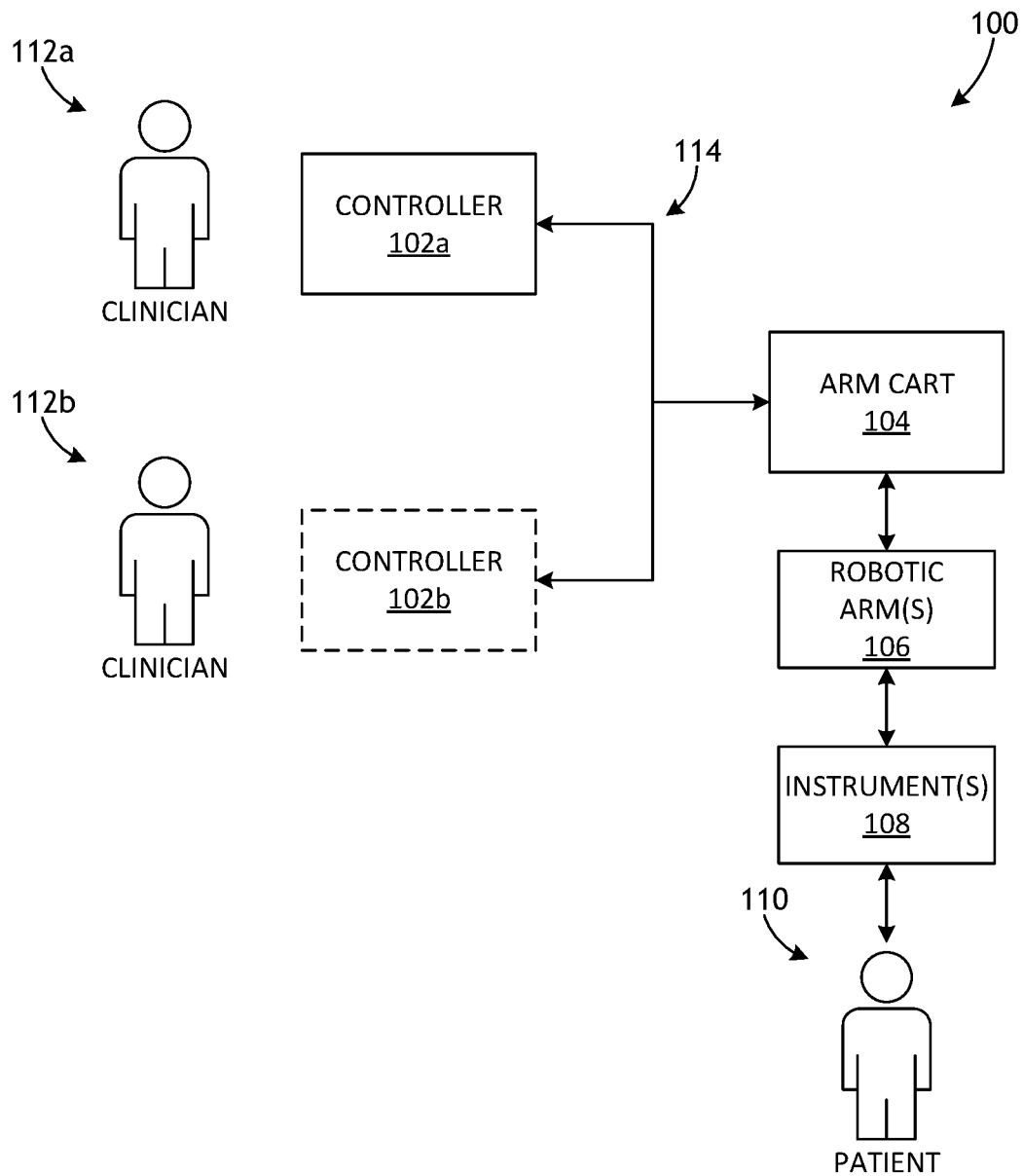
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications mean configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
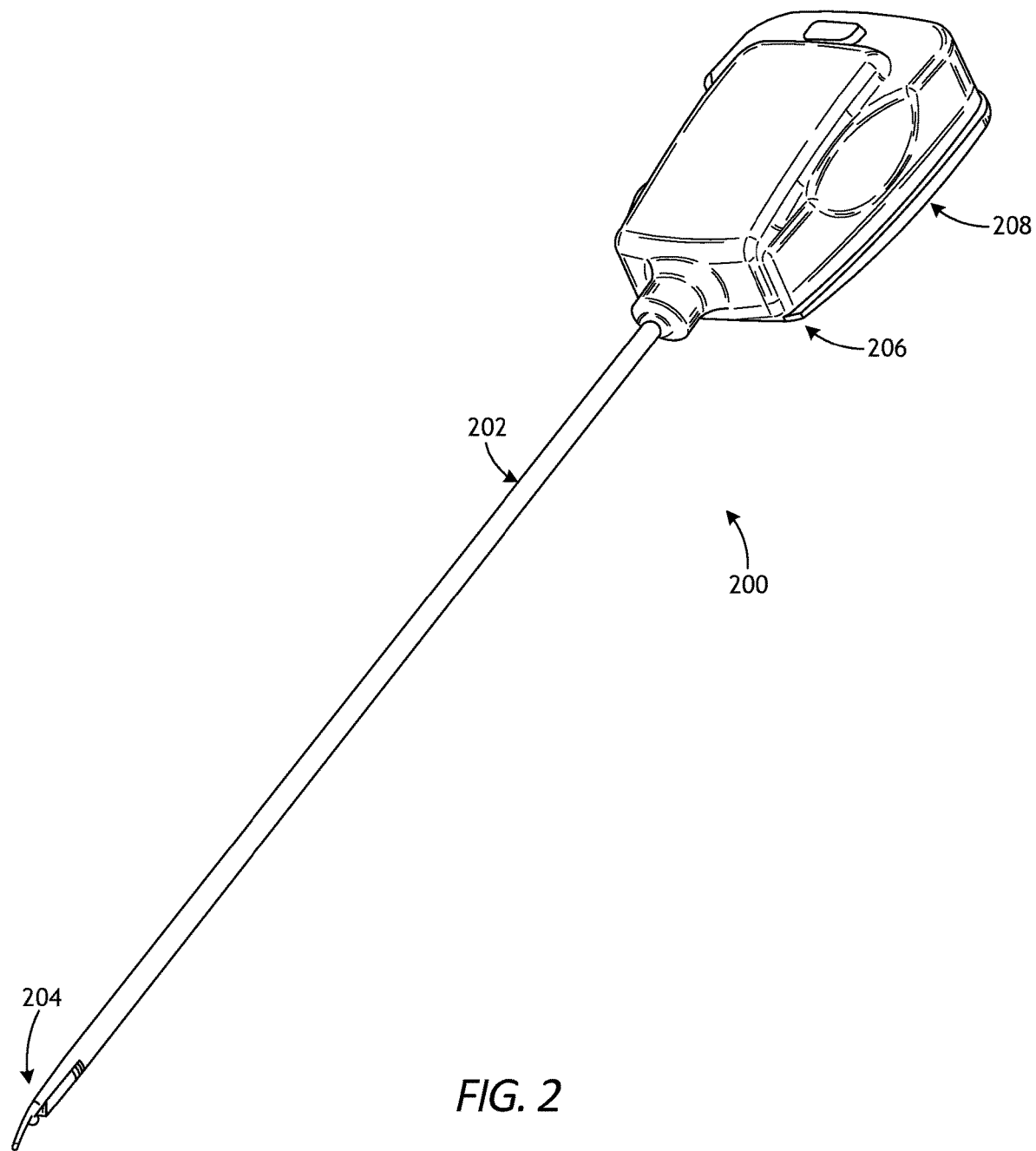
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
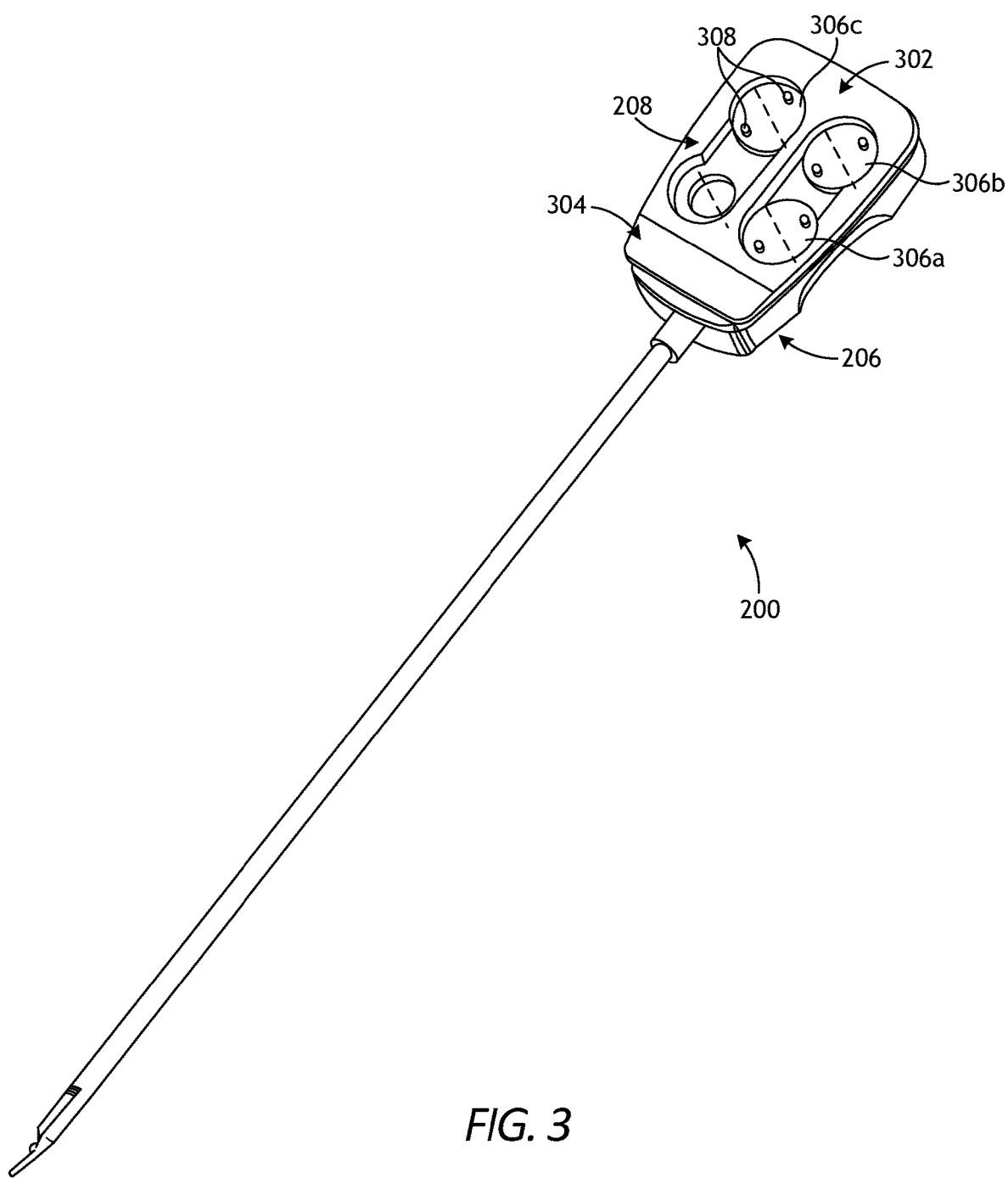
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
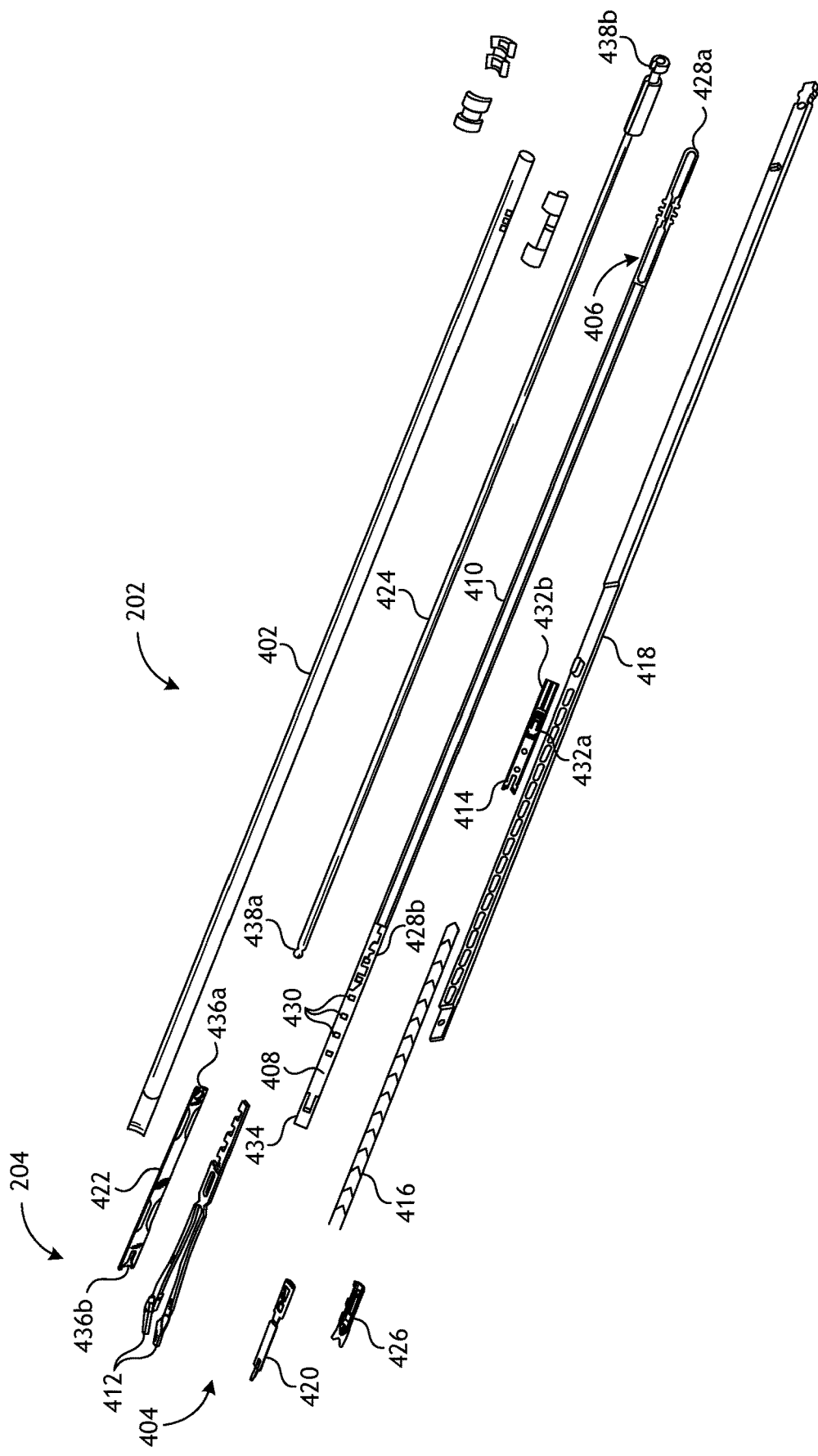
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 furthers include a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
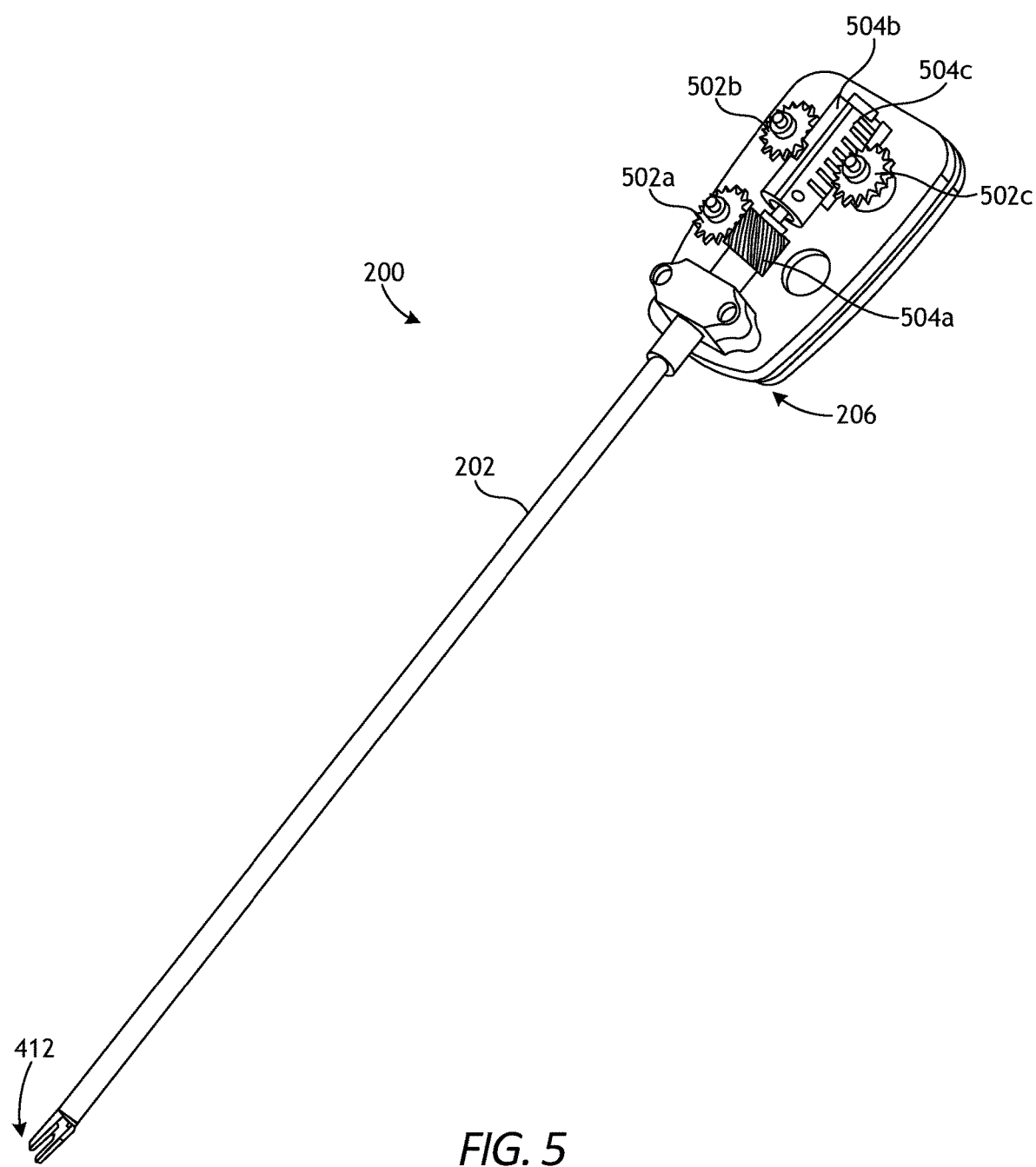
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
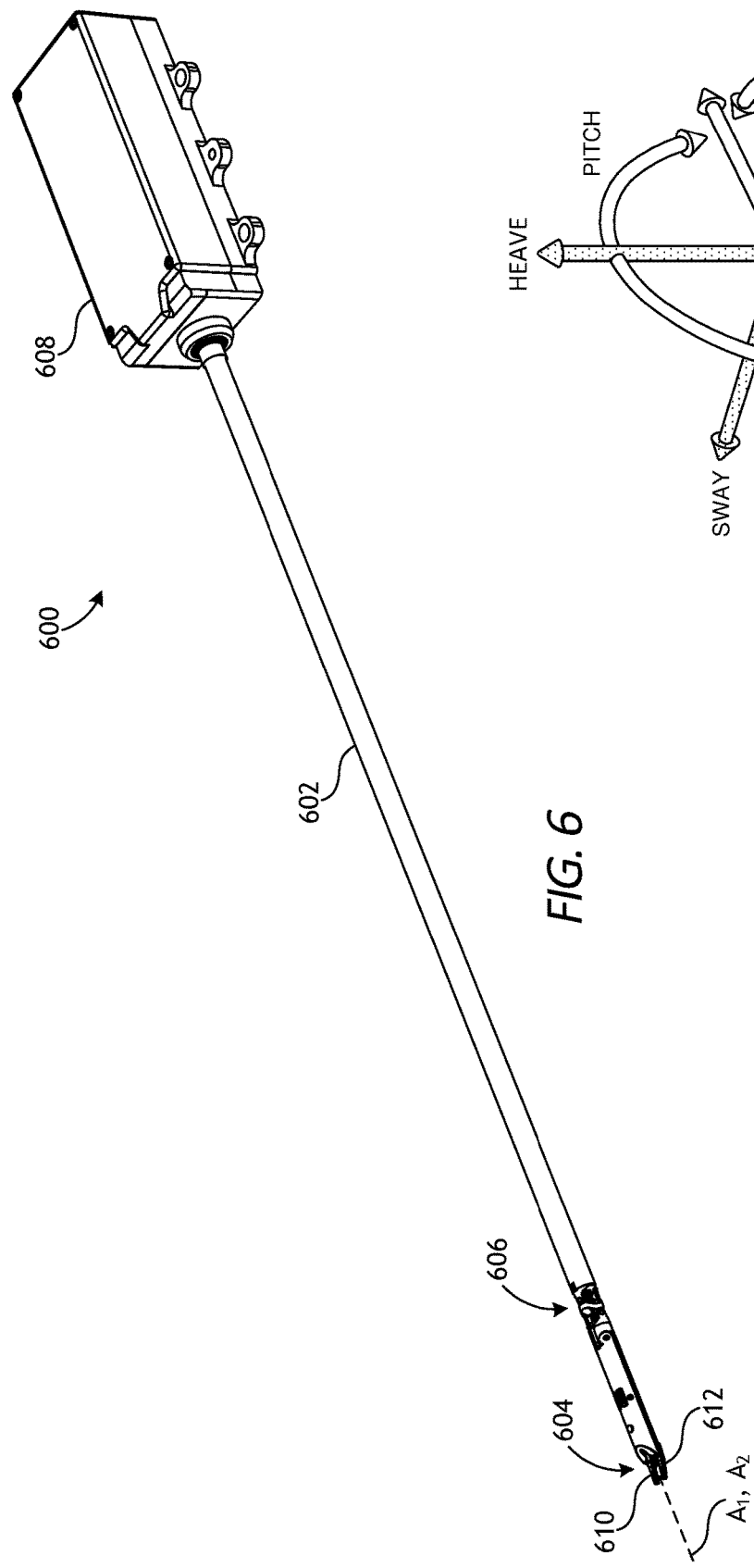
FIG. 6 is a side view of an example surgical tool that may incorporate some or all of the principles of the present disclosure.

FIG. 6 is an isometric top view of another example surgical tool 600 that may incorporate some or all of the principles of the present disclosure. Similar to the surgical tool 200 of FIG. 2, the surgical tool 600 may be used in conjunction with the robotic surgical system 100 of FIG. 1. As illustrated, the surgical tool 600 includes an elongate shaft 602, an end effector 604 positioned at the distal end of the shaft 602, a wrist 606 (alternately referred to as a "articulable wrist joint") that couples the end effector 604 to the distal end of the shaft 602, and a drive housing 608 coupled to the proximal end of the shaft 602. In some embodiments, the shaft 602, and hence the end effector 604 coupled thereto, is configured to rotate about a longitudinal axis $A_1$.

In the illustrated embodiment, the end effector 604 comprises a clip applier that includes opposing jaw members 610, 612 configured to collapse toward one another to crimp a surgical clip. The wrist 606 comprises an articulatable joint that facilitates pivoting movement of the end effector 604 relative to the shaft 602 to position the end effector 604 at desired orientations and locations relative to a surgical site. The housing 608 includes (contains) various actuation mechanisms designed to control articulation and operation of the end effector 604.

Figure 7:
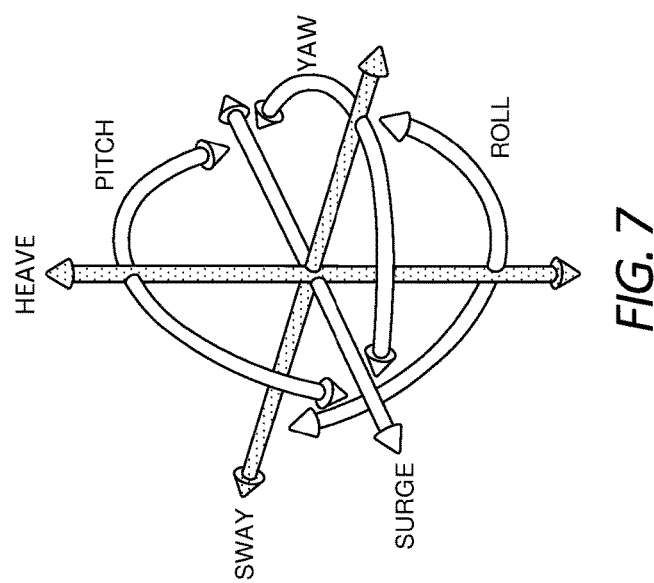
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane. SURGE Referring again to FIG. 6, the surgical tool 600 includes a plurality of drive cables (generally obscured in FIG. 6) that form part of a cable driven motion system configured to facilitate operation and articulation (movement) of the end effector 604 relative to the shaft 602. For example, selectively moving the drive cables can actuate the end effector 604 and thereby collapse the jaw members 610, 612 toward each other. Moreover, moving the drive cables can also move the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. In the articulated position, the longitudinal axes $A_1, A_2$ would be angularly offset from each other such that the end effector 604 is at a non-zero angle relative to the shaft 602.

Figure 8:
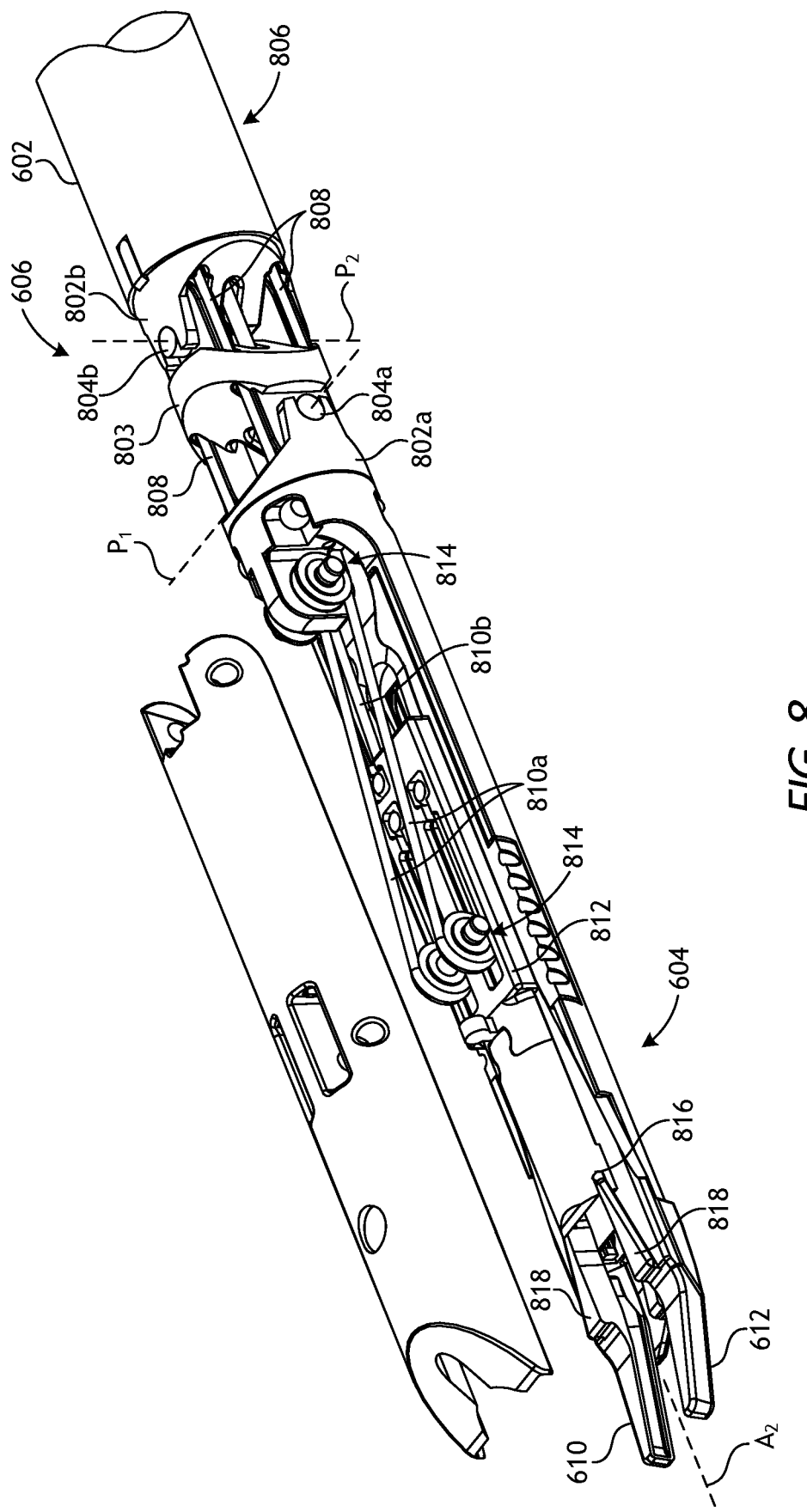
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts an enlarged and partially exploded view of the end effector 604 and the wrist 606. The wrist 606 operatively couples the end effector 604 to the shaft 602. To accomplish this, the wrist 606 includes a distal clevis 802a, a proximal clevis 802b, and a spacer 803 interposing the distal and proximal clevises 802a,b. The end effector 604 is coupled to the distal clevis 802a and the distal clevis 802a is rotatably mounted to the spacer 803 at a first axle 804a. The spacer 803 is rotatably mounted to the proximal clevis 802b at a second axle 804b and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "pitch" articulation of the end effector 604, and movement about the second pivot axis $P_2$ provides "yaw" articulation of the end effector 604.

A plurality of drive cables 808 extend longitudinally within the shaft 602 and pass through the wrist 106 to be operatively coupled to the end effector 604. The drive cables 808 form part of the cable driven motion system briefly described above, and may be referred to and otherwise characterized as cables, bands, lines, cords, wires, ropes, strings, twisted strings, elongate members, etc. The drive cables 808 can be made from a variety of materials including, but not limited to, metal (e.g., tungsten, stainless steel, etc.) or a polymer.

The drive cables 808 extend proximally from the end effector 604 to the drive housing 608 (FIG. 6) where they are operatively coupled to various actuation mechanisms or devices housed (contained) therein to facilitate longitudinal movement (translation) of the drive cables 808. Selective actuation of the drive cables 808 causes the end effector 604 to articulate (pivot) relative to the shaft 602. Moving a given drive cable 808 constitutes applying tension (i.e., pull force) to the given drive cable 808 in a proximal direction, which causes the given drive cable 808 to translate and thereby cause the end effector 604 to move (articulate) relative to the shaft 602.

One or more actuation cables 810, shown as first actuation cables 810a and second actuation cables 810b, may also extend longitudinally within the shaft 602 and pass through the wrist 106 to be operatively coupled to the end effector 604. The actuation cables 810a,b may be similar to the drive cables 808 and also form part of the cable driven motion system. Selectively actuating the actuation cables 810a,b causes the end effector 604 to actuate, such as collapsing the first and second jaw members 610, 612 to crimp a surgical clip (not shown).

More specifically, the actuation cables 810a,b may be operatively coupled to a cam 812 that is slidably engageable with the jaw members 610, 612. One or more pulleys 814 may be used to receive and redirect the first actuation cables 810a for engagement with the cam 812. Longitudinal movement of the first actuation cables 810a correspondingly moves the cam 812 distally relative to the jaw members 610, 612. The distal end of the cam 812 includes a tapering recess or camming channel 1204 formed therein for slidably receiving corresponding cam tracks 818 provided by the jaw members 610, 612. As the cam 812 is advanced distally, the camming channel 1204 pushes (collapses) the jaw members 610, 612 toward one another, thereby crimping a surgical clip (not shown) disposed therebetween. Actuation of the second actuation cables 810b (one shown) pulls the cam 812 proximally, thereby allowing the jaw members 610, 612 to open again to receive another surgical clip.

Although not expressly depicted in FIG. 8, an assembly including, for example, a feedbar, a feeder shoe, and a clip track may be included at or near the end effector 604 to facilitate feeding surgical clips into the jaw members 610, 612. In some embodiments, the feedbar (or a connecting member) may be flexible and extend through the wrist 606.

Figure 9:
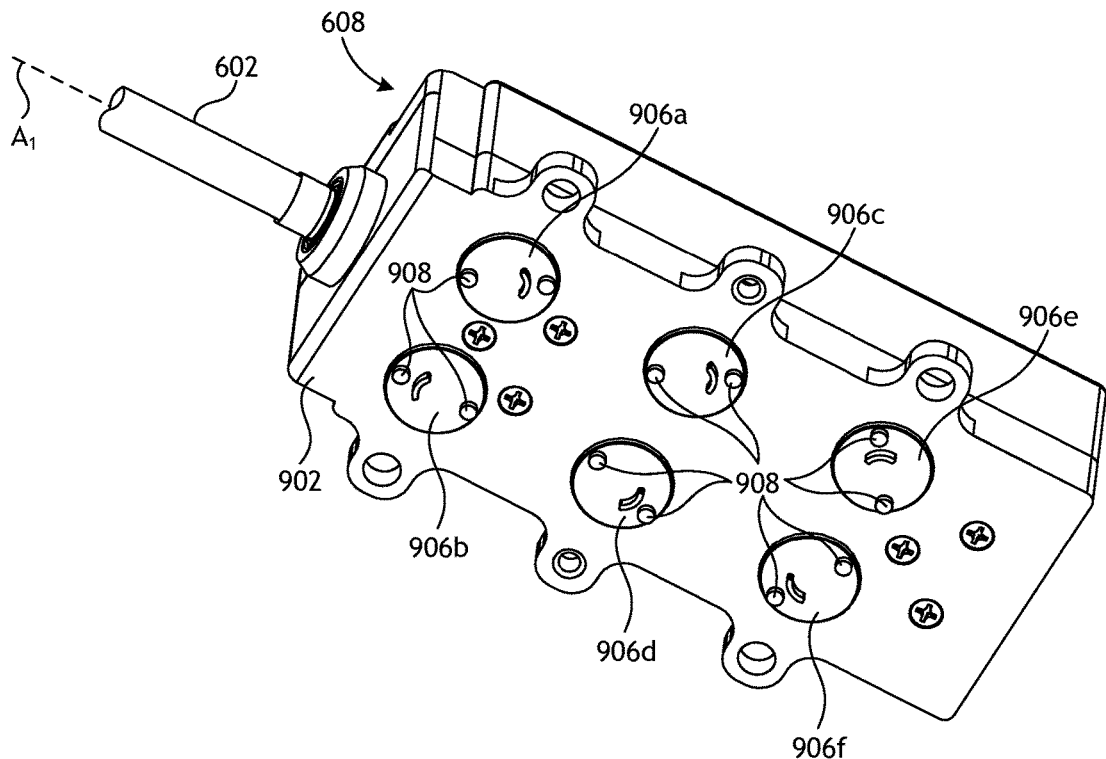
FIG. 9 is a bottom view of the drive housing of the surgical tool of FIG. 6.

FIG. 9 is a bottom view of the drive housing 608, according to one or more embodiments. As illustrated, the drive housing 608 may include a tool mounting interface 902 used to operatively couple the drive housing 608 to a tool driver of a robotic manipulator. The tool mounting interface 902 may mechanically, magnetically, and/or electrically couple the drive housing 608 to a tool driver.

As illustrated, the interface 902 includes and supports a plurality of drive inputs, shown as drive inputs 906a, 906b, 906c, 906d, 906e, and 906f. Each drive input 906a-f may comprise a rotatable disc configured to align with and couple to a corresponding input actuator (not shown) of a tool driver. Moreover, each drive input 906a-f provides or defines one or more surface features 908 configured to align with mating features provided on the corresponding input actuator. The surface features 908 can include, for example, various protrusions and/or indentations that facilitate a mating engagement.

In some embodiments, actuation of the first drive input 906a may control rotation of the elongate shaft 602 about its longitudinal axis $A_1$. Depending on the rotational actuation of the first drive input 906a, the elongate shaft 602 may be rotated clockwise or counter-clockwise. In some embodiments, selective actuation of the second and third drive inputs 906b,c may cause movement (axial translation) of the actuation cables 810a,b (FIG. 8), which causes the cam 812 (FIG. 8) to move and crimp a surgical clip, as generally described above. In some embodiments, actuation of the fourth drive input 906d feeds a surgical clip into the jaw members 610, 612 (FIG. 8). In some embodiments, actuation of the fifth and sixth drive inputs 906e,f causes movement (axial translation) of the drive cables 808 (FIG. 8), which results in articulation of the end effector 604. Each of the drive inputs 906a-f may be actuated based on user inputs communicated to a tool driver coupled to the interface 902, and the user inputs may be received via a computer system incorporated into the robotic surgical system.

Figure 10:
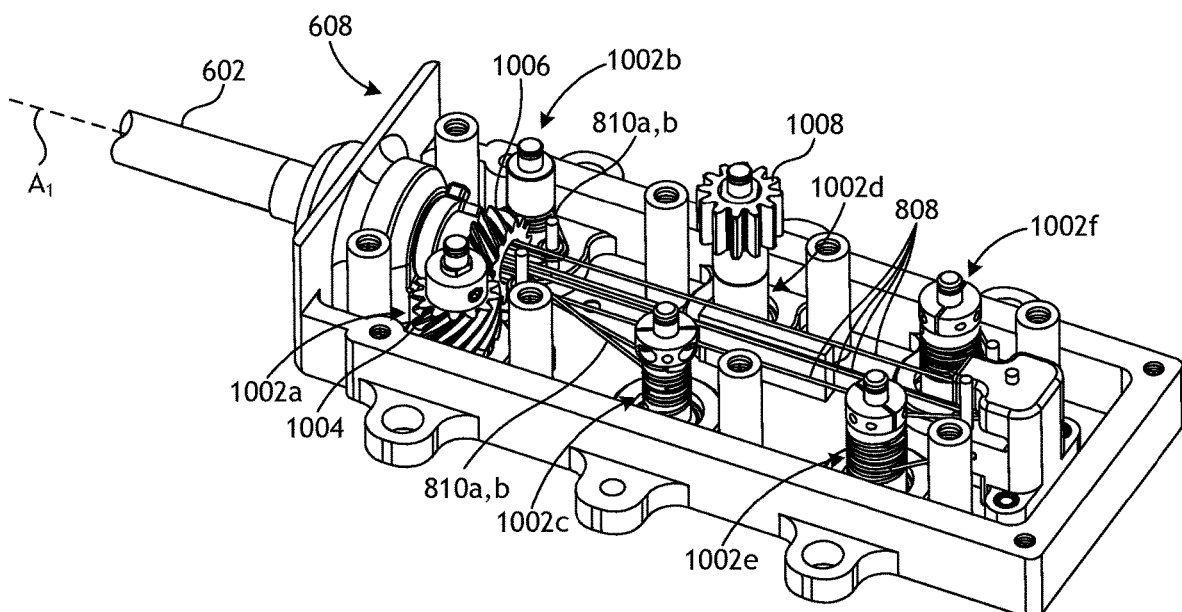
FIG. 10 is an isometric exposed view of the interior of the drive housing of the surgical tool of FIG. 6.

FIG. 10 is an isometric exposed view of the interior of the drive housing 608, according to one or more embodiments. Several component parts that may otherwise be contained within the drive housing 608 are not shown in FIG. 10 to enable discussion of the depicted component parts.

As illustrated, the drive housing 608 contains a first capstan 1002a, which is operatively coupled to or extends from the first drive input 906a (FIG. 9) such that actuation of the first drive input 906a results in rotation of the first capstan 1002a. A helical drive gear 1004 is coupled to or forms part of the first capstan 1002a and is configured to mesh and interact with a driven gear 1006 operatively coupled to the shaft 602 such that rotation of the driven gear 1006 correspondingly rotates the shaft 602. Accordingly, rotation of the helical drive gear 1004 (via actuation of the first drive input 906a of FIG. 9) will drive the driven gear 1006 and thereby control rotation of the elongate shaft 602 about the longitudinal axis $A_1$.

The drive housing 608 also includes second and third capstans 1002b and 1002c operatively coupled to or extending from the second and third drive inputs 906b,c (FIG. 9), respectively, such that actuation of the second and third drive inputs 906b,c results in rotation of the second and third capstans 1002b,c. The second and third capstans 1002b,c comprise capstan pulleys operatively coupled to the actuation cables 810a,b (FIG. 8) such that rotation of a given capstan 1002b,c actuates (longitudinally moves) a corresponding one of the actuation cables 810a,b. Accordingly, selective rotation of the second and third capstans 1002b,c via actuation of the second and third drive inputs 906b,c, respectively, will cause movement (axial translation) of the actuation cables 810a,b, which causes the cam 812 (FIG. 8) to move and crimp a surgical clip.

The drive housing 608 further includes a fourth capstan 1002d, which is operatively coupled to or extends from the fourth drive input 906d (FIG. 9) such that actuation of the fourth drive input 906d results in rotation of the fourth capstan 1002d. A spur gear 1008 is coupled to or forms part of the fourth capstan 1002d and is configured to mesh and interact with a rack gear (not shown) also contained within the drive housing 608. The rack gear may be operatively coupled to a feedbar (or another connecting member) which facilitates operation of a feeder shoe and associated clip track to feed surgical clips into the jaw members 610, 612 (FIGS. 6 and 8). Accordingly, rotation of the spur gear 1008 (via actuation of the fourth drive input 906d) will control the feedbar and thereby control loading of surgical clips into the jaw members 610, 612 as desired.

The drive housing 608 further contains or houses fifth and sixth capstans 1002e and 1002f operatively coupled to or extending from the fifth and sixth drive inputs 906e,f (FIG. 9), respectively, such that actuation of the fifth and sixth drive inputs 906e,f results in rotation of the fifth and sixth capstans 1002e,f. The fifth and sixth capstans 1002e,f comprise capstan pulleys operatively coupled to the drive cables 808 (FIG. 8) such that rotation of a given capstan 1002e,f actuates (longitudinally moves) a corresponding one of the actuation cables 808. Accordingly, selective rotation of the fifth and sixth capstans 1002e,f via actuation of the fifth and sixth drive inputs 906e,f, respectively, will cause movement (axial translation) of the drive cables 808 and thereby articulate (pivot) the end effector 604 relative to the shaft 602.

The surgical tools 200, 600 described herein above may incorporate and facilitate the principles of the present disclosure in improving feeding and/or forming of surgical clips in robotic or non-robotic clip appliers. Moreover, it is contemplated herein to combine some or all of the features of the surgical tools 200, 600 to facilitate operation of the embodiments described below. Accordingly, example surgical tools that may incorporate the principles of the present disclosure may include geared actuators, capstan pulley and cable actuators, or any combination thereof, without departing from the scope of the disclosure.

Figure 11A:
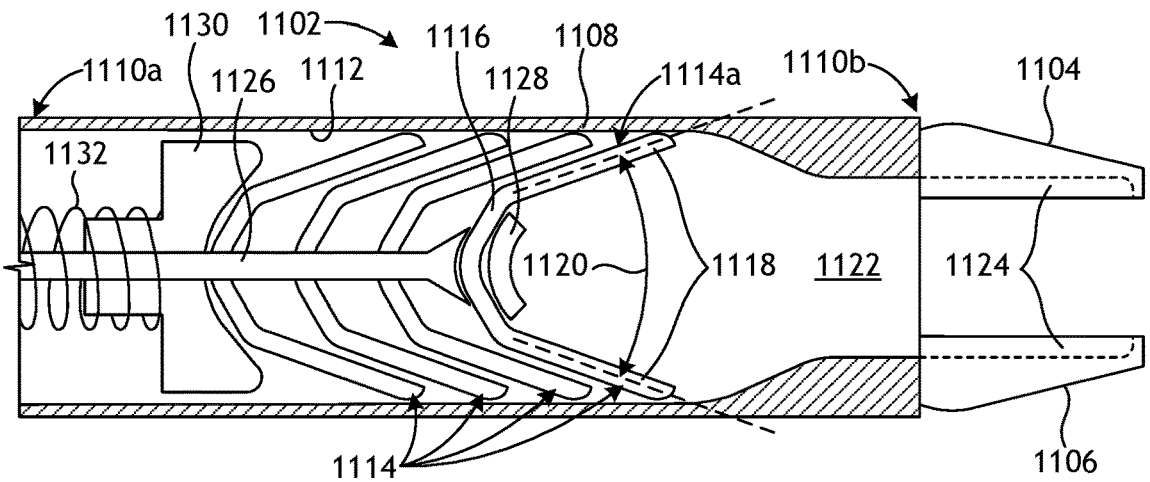
FIGS. 11A-11C are partial cross-sectional top views of a portion of an example end effector.
Figure 11B:
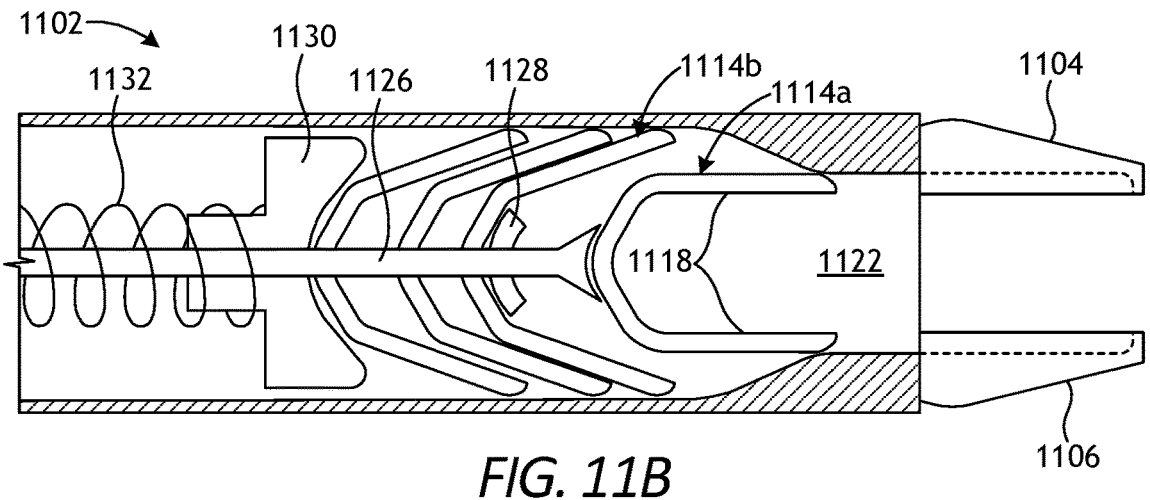
Figure 11C:
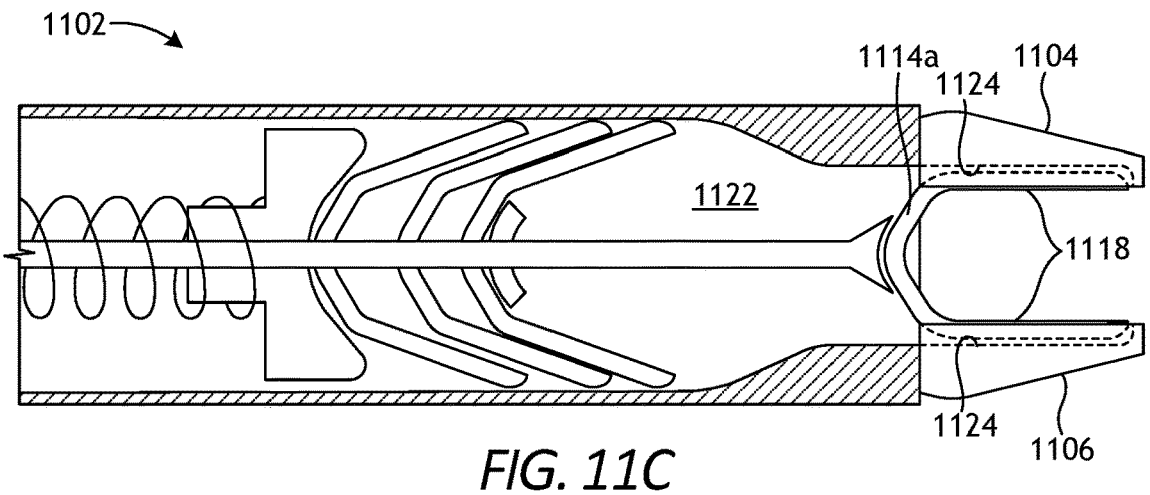

FIGS. 11A-11C are partial cross-sectional top views of a distal portion of an example end effector 1102, according to one or more embodiments of the present disclosure. The end effector 1102 may be similar in some respects to the end effectors 204 and 604 of FIGS. 2 and 6, respectively. For instance, similar to the end effectors 204, 604, the end effector 1102 may be incorporated into either or both of the surgical tools 200, 600 described herein above. Moreover, the end effector 1102 may comprise a clip applier having opposed jaw members 1104 and 1106 actuatable to collapse toward one another to crimp a surgical clip. As described herein, the end effector 1102 may incorporate various component parts and actuatable mechanisms or features that facilitate the feeding of surgical clips into the jaw members 1104, 1106 and collapsing the jaw members 1104, 1106 to crimp the surgical clip when desired.

FIGS. 11A-11C illustrate progressive views of the end effector 1102 during example operation of feeding the surgical clips 1114 into the jaw members 1104, 1106. Referring first to FIG. 11A, the end effector 1102 includes an elongate body 1108 having a proximal end 1110a and a distal end 1110b. In some embodiments, the body 1108 may be the same as or similar to the outer tube 402 of FIG. 4. In other embodiments, however, the body 1108 may comprise an independent structure from the outer tube 402. Various component parts and mechanisms of the end effector 1102 are positioned within the inside or interior of the body 1108. The jaw members 1104, 1106 extend out of or otherwise protrude from the distal end 1110b of the body 1108. In at least one embodiment, the proximal end 1110a may be operatively coupled to an elongate shaft of a surgical tool, such as the shaft 202 of the surgical tool 200 of FIG. 2. In other embodiments, however, the proximal end 1110a may be operatively coupled to an articulable wrist joint, such as the wrist 606 of the surgical tool 600 of FIG. 6. In such embodiments, the surgical clips 1114 are stored distal to the wrist within the end effector 1102.

The end effector 1102 also includes a clip track 1112. In some embodiments, the body 1108 defines or otherwise provides the clip track 1112. In other embodiments, however, the clip track 1112 may comprise a separate structural component that is removably positioned within the body 1108. The clip track 1112 may be configured to contain and otherwise house one or more surgical clips 1114, and preferably a plurality of surgical clips 1114 arranged in series. While four surgical clips 1114 are depicted in FIG. 11A, more or less than four may be employed, without departing from the scope of the disclosure.

Each surgical clip 1114 includes a crown 1116 (alternately referred to as an "apex") and a pair of legs 1118 extending longitudinally from the crown 1116. The legs of conventional surgical clips typically converge toward one another. Converging legs, however, reduce the clip-to-jaw retention capability and also reduce allowable tip width between the jaw members 1104, 1106, which correspondingly limits the size of tissue that can be treated with the end effector 1102. Moreover, with converging clip legs, the surgical clips are commonly arranged with the legs of the more proximal surgical clips engaging the crown of the more distal surgical clips, which maximizes the axial space accommodated by the surgical clips in the clip track and thereby reduces the number of clips that can be stored for use.

In contrast, the surgical clips 1114 described herein may be characterized as "wide-aperture" surgical clips. More specifically, the legs 1118 of the surgical clips 1114 diverge from each other and otherwise open to a diverging opening angle 1120 relative to one another. The diverging opening angle 1120 may comprise any angle that results in the legs 1118 diverging from each other as extending from the crown 1116. The diverging opening angle 1120 may range between about 5° and about 35°, but could be as large as 45° or more, depending on the design constraints of the clip track 1112.

The diverging opening angle 1120 may prove advantageous in allowing the surgical clips 1114 to be positioned within the clip track 1112 in a partially or fully nested configuration, where the legs 1118 of the more proximal surgical clips 1114 extend past the crown 1116 and partially overlap the legs 1118 of the more distal surgical clips 1114. Consequently, the more distal surgical clips 1114 are received by and partially nested within the more proximal distal clips 1114. As will be appreciated, this nested configuration allows the clip track 1112 to accommodate a higher number of surgical clips 1114 within the same axial constraints (dimensions), which provides a user with additional surgical clips 1114 for use.

Surgical clips 1114 with legs 1118 that diverge at the diverging opening angle 1120 are referred to herein as being in a first or "wide" state. To be received between the jaw members 1104, 1106 for crimping, however, the surgical clips 1114 must be transitioned from the wide state to a second or "tissue-ready" state. To accomplish this, the end effector 1102 may include a pre-forming region 1122 configured to receive wide state surgical clips 1114 and reduce (minimize) the diverging opening angle 1120 as the surgical clips 1114 advance distally such that tissue ready surgical clips 1114 are discharged into the jaw members 1104, 1106. The surgical clips 1114 may be plastically or elastically deformed as they traverse the pre-forming region 1122 in the distal direction. The surgical clips 1114 are fully formed when the jaw members 1104, 1106 collapse and crimp the surgical clips 1114.

As used herein, "minimizing" the diverging opening angle 1120 refers to decreasing the diverging opening angle 1120 to an angular magnitude where the surgical clip 1114 can be received in between the jaw members 1104, 1106. In at least one embodiment, "minimizing" the diverging opening angle 1120 refers to eliminating the diverging opening angle 1120 such that the legs 1118 extend parallel or substantially parallel to one another.

The pre-forming region 1122 generally comprises opposed structural surfaces that converge or taper toward one another in the distal direction. In some embodiments, the pre-forming region 1122 may be defined by the body 1108. In other embodiments, however, the pre-forming region 1122 may be defined or otherwise provided by the clip track 1112.

The distal end of the pre-forming region 1122 may be aligned with and arranged to feed tissue-ready surgical clips 1114 into the jaw members 1104, 1106. In at least one embodiment, each jaw member 1104, 1106 includes a channel or groove 1124 formed on opposed inner surfaces thereof for receiving a distal-most surgical clip, referenced herein as 1114a. In such embodiments, the grooves 1124 may prove advantageous in helping to capture and maintain the distal-most surgical clip 1114a in a known and secure position between the jaw members 1104, 1106. In other embodiments, however, the grooves 1124 may be omitted and the distal-most surgical clip 1114a may instead be captured or held between the jaw members 1104, 1106 via an interference fit or the like.

The end effector 1102 may further include a feedbar 1126, a retention member 1128, and a feeder shoe 1130. The feedbar 1126 may be configured to engage and move the distal-most surgical clip 1114a through the pre-forming region 1122 and deliver the distal-most surgical clip 1114 in its tissue-ready state to the jaw members 1104, 1106. In some embodiments, the feedbar 1126 may extend to the end effector 1102 from a drive housing (e.g., the drive housings 206, 606 of FIGS. 2 and 6, respectively). At the drive housing, the feedbar 1126 may be operatively coupled to an actuating mechanism or device configured to cause longitudinal translation of the feedbar 1126. In one embodiment, for example, the feedbar 1126 may be operatively coupled to and otherwise extend from one or more translatable driven gears, such as the first and second driven gears 504a,b of FIG. 5. In embodiments with an articulable wrist, the feedbar 1126 may be made of a flexible material and extend through the wrist. Alternatively, the feedbar 1126 may be operatively coupled to a cable-driven worm gear arranged distal to the wrist and the associated drive cable(s) that moves the worm gear extend through the wrist.

The retention member 1128 may be configured to engage the distal-most surgical clip 1114a and thereby prevent the stacked surgical clips 1114 from advancing distally until the distal-most surgical clip 1114a is acted upon by the feedbar 1126. In some embodiments, the retention member 1128 may comprise a passive biasing device, such as a gate spring or the like. In such embodiments, the spring force of the retention member 1128 may be sufficient to retain the stacked surgical clips 1114 in place, but may be overcome when the feedbar 1126 applies an axial load on the distal-most surgical clip 1114a. In other embodiments, however, the retention member 1128 may comprise a post or the like operatively coupled to an actuatable device or mechanism. The post may be configured to retain the stacked surgical clips 1114 in place and release the distal-most surgical clip 1114a when actuated. In such embodiments, the retention member 1128 may be actuated and otherwise driven using any of the actuation components associated with the drive housings 206, 606 (FIGS. 2 and 6, respectively) discussed herein, or alternatively may be operatively coupled to a cable-driven worm gear or the like arranged near the end effector 1102.

The feeder shoe 1130 may be configured to apply an axial load in the distal direction on the surgical clips 1114 positioned within the clip track 1112. The axial load helps maintain proper positioning and sequential feeding of the surgical clips 1114. In some embodiments, as illustrated, the feeder shoe 1130 may include a compression spring 1132 that engages a proximal end of the feeder shoe 1130 to provide a passive and constant axial load on the surgical clips 1114. In other embodiments, however, the feeder shoe 1130 may include or comprise an actuatable device or mechanism that selectively supplies the axial load. In such embodiments, the feeder shoe 1130 may apply the axial load only to advance the surgical clips 1114 a predetermined distance within the clip track 1112.

With additional reference to FIGS. 11B and 11C, example operation of feeding the distal-most surgical clip 1114a into the jaw members 1104, 1106 is now provided. In FIG. 11A, the retention member 1128 is shown engaging the distal-most surgical clip 1114a and thereby preventing the stacked surgical clips 1114 from advancing distally until acted upon by the feedbar 1126. In some embodiments, as illustrated, the retention member 1128 may engage the distal-most surgical clip 1114a at or near the crown 1116. In other embodiments, however, the retention member 1128 may engage the distal-most surgical clip 1114a at any other location or may alternatively engage the entire stack of surgical clips 1114, without departing from the scope of the disclosure.

To advance the distal-most surgical clip 1114a toward the jaw members 1104, 1106, the feedbar 1126 may be advanced distally until engaging the distal-most surgical clip 1114a. In some embodiments, as illustrated, the feedbar 1126 may engage the distal-most surgical clip 1114a at or near the crown 1116, but could alternatively engage the distal-most surgical clip 1114a at any other location. In embodiments where the retention member 1128 comprises a passive spring, an axial load provided by the feedbar 1126 on the distal-most surgical clip 1114a may overcome the spring force of the retention member 1128 to bypass the retention member 1128 and thereby move the distal-most surgical clip 1114a distally. In other embodiments, however, the retention member 1128 may be actuated or otherwise moved to allow the feedbar 1126 to convey the distal-most surgical clip 1114a distally past the retention member 1128.

In FIG. 11B, the distal-most surgical clip 1114a is shown being advanced distally by the feedbar 1126 past the retention member 1128 and into the pre-forming region 1122. Once the distal-most surgical clip 1114a bypasses the retention member 1128, the feeder shoe 1130 may distally advance the remaining surgical clips 1114 positioned within the clip track 1112 until a penultimate surgical clip 1114b is received and retained by the retention member 1128. In some embodiments, the compression spring 1132 may provide the required axial load to move the surgical clips 1114 distally, but in other embodiments, the feeder shoe 1130 may be actuated to advance the surgical clips 1114 a predetermined distance.

As the distal-most surgical clip 1114a is advanced distally, the legs 1118 are received by and slidably engage the inner walls of the pre-forming region 1122. The distally converging and ramped configuration of the pre-forming region 1122 transitions the distal-most surgical clip 1114a from the first or "wide" state to the second or "tissue-ready" state in preparation for being received by the jaw members 1104, 1106. As it traverses the pre-forming region 1122, the distal-most surgical clip 1114a plastically or elastically deforms as the diverging opening angle 1120 (FIG. 11A) of the legs 1118 is reduced or minimized.

In FIG. 11C, the distal-most surgical clip 1114a is shown as having traversed the pre-forming region 1122 and being received within the jaw members 1104, 1106. In embodiments including the grooves 1124 defined on each jaw member 1104, 1106, the legs 1118 may spring outward and seat themselves within the grooves 1124, which may help retain the surgical clip 1114 in place. Otherwise, the distal-most surgical clip 1114 may be retained between the jaw members 1104, 1106 via an interference. At this point, the jaw members 1104, 1106 may be actuated to collapse or close and thereby crimp the distal-most surgical clip 1114a therebetween. As used herein, "actuating" the jaw members 1104, 1106 refers to the mechanical process of collapsing or closing the jaw members 1104, 1106.

Figure 12A:
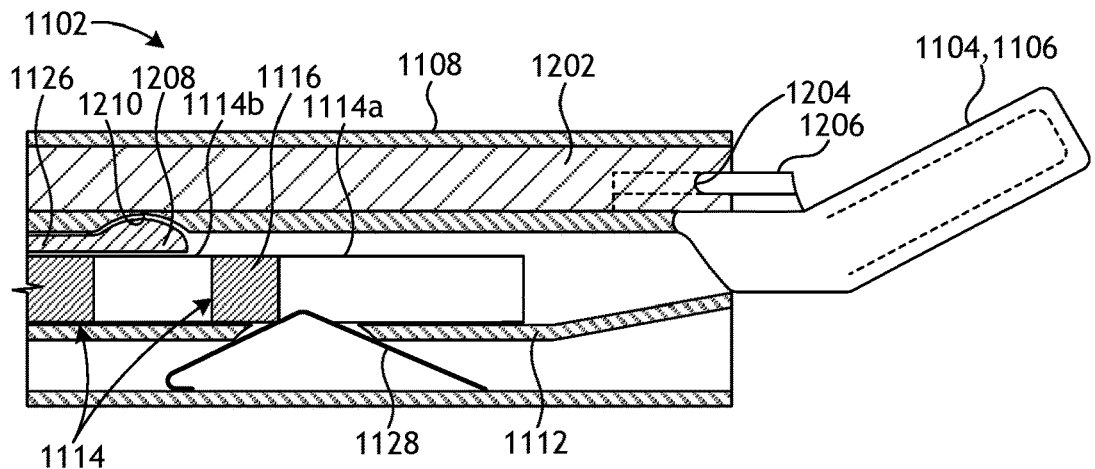
FIGS. 12A-12C are partial cross-sectional side views of the end effector of FIGS. 11A-11C.
Figure 12B:
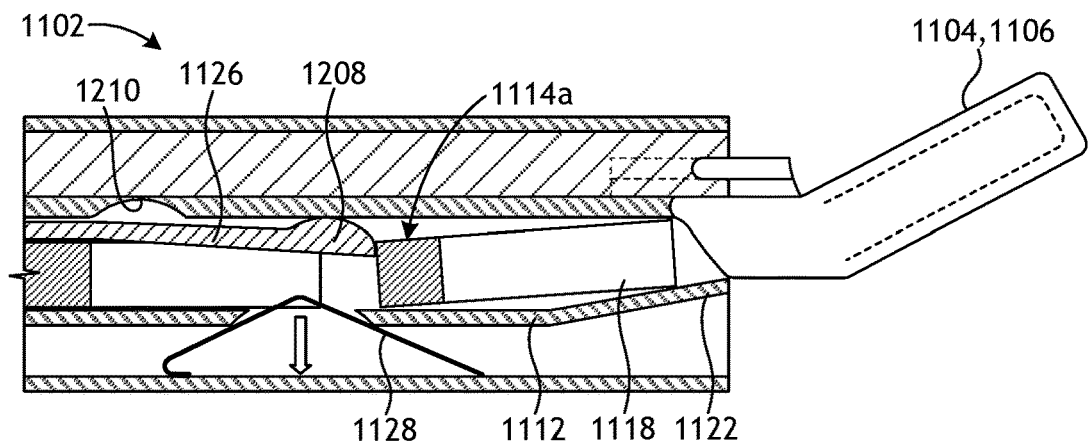
Figure 12C:
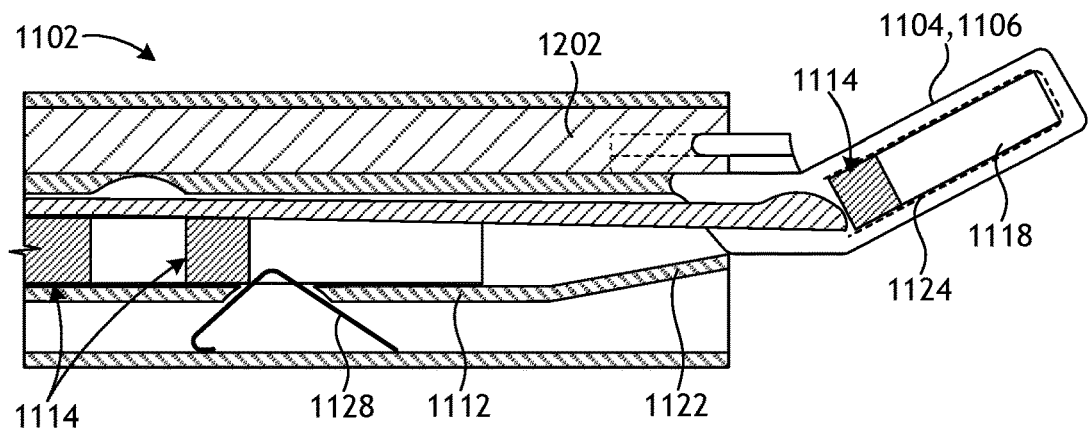

FIGS. 12A-12C are partial cross-sectional side views of the end effector 1102 of FIGS. 11A-11C. Similar to FIGS. 11A-11C, FIGS. 12A-12C provide progressive views of the end effector 1102 during example operation of feeding the distal-most surgical clip 1114a into the jaw members 1104, 1106.

Referring first to FIG. 12A, the end effector 1102 may further include a cam 1202 that is slidably engageable with the jaw members 1104, 1106. In the illustrated embodiment, the cam 1202 is arranged within the body 1108, but can alternatively be arranged external to the body 1108, without departing from the scope of the disclosure. The cam 1202 may be movable relative to the body 1108 and, more importantly, to the jaw members 1104, 1106. The distal end of the cam 1202 includes a tapering recess or camming channel 1204 formed therein for slidably receiving corresponding cam tracks 1206 provided by each jaw member 1104, 1106. As the cam 1202 is actuated and advanced distally, the camming channel 1204 slidably engages the cam tracks 1206 provided and thereby pushes (collapses) the jaw members 1104, 1106 toward one another.

As illustrated, the surgical clips 1114 are shown arranged within the clip track 1112 with the distal-most surgical clip 1114a at least partially nested within the penultimate surgical clip 1114b. Moreover, the retention member 1128 is depicted as engaging the distal-most surgical clip 1114a to prevent the stacked surgical clips 1114 from advancing distally. In the illustrated embodiment, the retention member 1128 is depicted as a passive gate spring that engages the distal-most surgical clip 1114a at or near its crown 1116. The retention member 1128 exhibits a spring force sufficient to retain the stacked surgical clips 1114 in place until the distal-most surgical clip 1114a is acted upon by the feedbar 1126.

In some embodiments, the feedbar 1126 may provide or otherwise define a protrusion 1208 at its distal end configured to mate with a groove 1210 defined in the clip track 1112 or the body 1108. Applying an axial load in the distal direction on the feedbar 1126 disengages the protrusion 1208 from the groove 1210, following which the feedbar 1126 may be advanced distally until engaging the distal-most surgical clip 1114a.

In FIG. 12B, the distal-most surgical clip 1114a is shown being advanced distally by the feedbar 1126 within the clip track 1112 and past the retention member 1128. More specifically, once the protrusion 1208 exits the groove 1210, the protrusion 1208 slidably engages the inner wall of the clip track 1112 and causes the distal end of the feedbar 1126 to flex downward and into engagement with the distal-most surgical clip 1114a. In the illustrated embodiment, the feedbar 1126 applies an axial load on the distal-most surgical clip 1114a that causes the retention member 1128 to flex downward and out of the way. As the distal-most surgical clip 1114a is advanced distally, the legs 1118 are received by and slidably engage the inner (lateral) walls of the pre-forming region 1122, which transitions the distal-most surgical clip 1114a from the wide state to the tissue-ready state in preparation for being received by the jaw members 1104, 1106.

In FIG. 12C, after the distal-most surgical clip 1114a bypasses the retention member 1128, the feeder shoe 1130 (FIGS. 11A-11C) may operate to advance the remaining surgical clips 1114 distally within the clip track 1112 until the penultimate surgical clip 1114b is received and retained by the retention member 1128. The distal-most surgical clip 1114a is shown in FIG. 12C as having traversed the pre-forming region 1122 and advanced into the jaw members 1104, 1106. In embodiments including the grooves 1124 defined on each jaw member 1104, 1106, the legs 1118 may spring outward and seat themselves within the grooves 1124. With the distal-most surgical clip 1114a properly seated within the jaw members 1104, 1106, the cam 1202 may then be actuated to collapse the jaw members 1104, 1106 and thereby crimp the distal-most surgical clip 1114a therebetween, as generally described above.

FIGS. 13A-13E are partial cross-sectional top views of a distal portion of another example end effector 1302, according to one or more embodiments of the present disclosure. The end effector 1302 may be similar in some respects to the end effector 1102 of FIGS. 11A-11C and, therefore, may be best understood with reference thereto, where like numerals will correspond to like components not described again in detail. FIGS. 13A-13E illustrate progressive views of the end effector 1302 during example operation of feeding surgical clips 1114 into the jaw members 1104, 1106 for crimping.

Figure 13A:
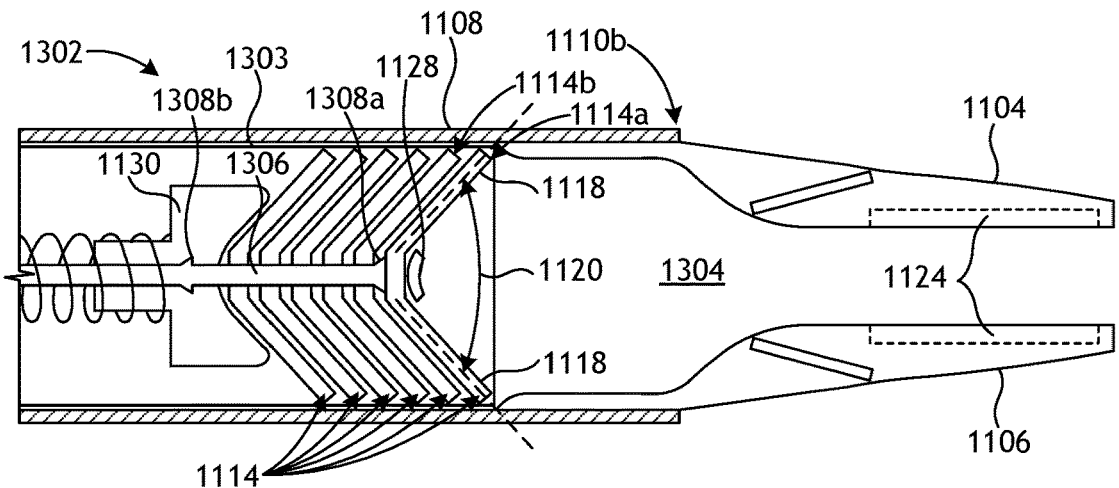
FIGS. 13A-13E are partial cross-sectional top views of a distal portion of another example end effector.

Referring first to FIG. 13A, the end effector 1302 includes the elongate body 1108 and the jaw members 1104, 1106 extend out of or otherwise protrude from the distal end 1110b thereof. A clip track 1303 is arranged within the body 1108 and is configured to contain and otherwise house the surgical clips 1114. While six surgical clips 1114 are depicted in FIG. 13A, more or less than six may be employed, without departing from the scope of the disclosure.

As with the prior embodiment, the legs 1118 of the surgical clips 1114 diverge from each other at the diverging opening angle 1120. However, the diverging opening angle 1120 depicted in FIG. 13A is greater than the diverging opening angle 1120 of FIG. 11A. Consequently, more surgical clips 1114 may be accommodated within the limited axial constraints (dimensions) of the clip track 1303 as the surgical clips 1114 are able to be positioned in a more nested configuration as compared with the surgical clips 1114 of FIGS. 11A-11C.

To transition the distal-most surgical clip 1114a from the first or "wide" state to the second or "tissue-ready" state, the distal-most surgical clip 1114a may be advanced into a pre-forming region 1304 configured to reduce (minimize) the diverging opening angle 1120 such that the distal-most surgical clip 1114a is provided to the jaw members 1104, 1106 in its tissue-ready state. As illustrated, the pre-forming region 1304 may be provided or otherwise defined by the jaw members 1104, 1106. More specifically, the pre-forming region 1304 may be arranged proximal to the distal end of the jaw members 1104, 1106 and may be characterized as or otherwise form part of a first stage that plastically or elastically deforms the distal-most surgical clip 1114a from the wide state to the tissue-ready state. The distal-most surgical clip 1114a is then advanced distally into the jaw members 1104, 1106 and to a second stage where it may be crimped when the jaw members 1104, 1106 collapse (close) toward one another. The pre-forming region 1304 may be aligned with and arranged to feed tissue-ready surgical clips 1114 into the jaw members 1104, 1106, each of which may include the channel or groove 1124 formed on opposed inner surfaces thereof.

The end effector 1302 further includes a feedbar 1306, which may comprise a two-stage feedbar configured to simultaneously engage and move the distal-most surgical clip 1114a and the penultimate surgical clip 1114b. To accomplish this, the feedbar 1306 provides a first engagement member 1308*a* and a second engagement member 1308*b*, alternately referred to as distal and proximal teeth, respectively. As illustrated, the first engagement member 1308*a* is located at the distal end of the feedbar 1306 and the second engagement member 1308*b* is located proximal to the first engagement member 1308*a* and axially offset therefrom a predetermined distance. As described below, the first and second engagement members 1308*a,b* may be configured to cooperatively and sequentially advance the distal-most and penultimate surgical clips 1114*a,b* into the pre-forming region 1304 and the jaw members 1104, 1106 in a two stage process.

The end effector 1302 may also include the retention member 1128, and the feeder shoe 1130, which operate as generally described above.

With additional reference to FIGS. 13B-13E, example operation of feeding the surgical clips 1114 into the jaw members 1104, 1106 is now provided. In FIG. 13A, the retention member 1128 is shown engaging the distal-most surgical clip 1114*a* and thereby preventing the stacked surgical clips 1114 from advancing distally. To distally advance the distal-most surgical clip 1114*a*, the feedbar 1306 may be advanced until the first engagement member 1308*a* engages the distal-most surgical clip 1114*a*. In embodiments where the retention member 1128 comprises a passive spring, an axial load provided by the feedbar 1306 on the distal-most surgical clip 1114*a* may overcome the spring force of the retention member 1128 to move the distal-most surgical clip 1114*a* distally and into the pre-forming region 1304. In other embodiments, however, the retention member 1128 may be actuated or otherwise moved to allow the feedbar 1306 to distally move the distal-most surgical clip 1114*a*.

Figure 13B:
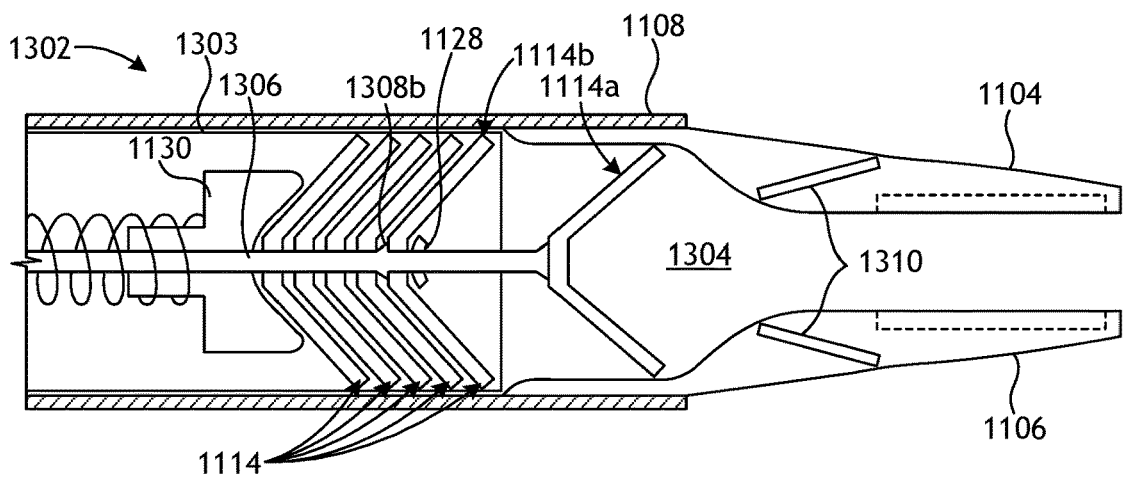

In FIG. 13B, the distal-most surgical clip 1114*a* is shown as having advanced distally past the retention member 1128 and into the pre-forming region 1304. Once the distal-most surgical clip 1114*a* bypasses the retention member 1128, the feeder shoe 1130 may operate to distally advance the remaining surgical clips 1114 positioned within the clip track 1303 until the penultimate surgical clip 1114*b* is received and retained by the retention member 1128. In some embodiments, advancing the distal-most surgical clip 1114*a* into the pre-forming region 1304 may also advance the second engagement member 1308*b* of the feedbar 1306 into engagement with the penultimate surgical clip 1114*b* as retained by the retention member 1128.

The distal-most surgical clip 1114*a* is received into the pre-forming region 1304 in its wide state. To transition the distal-most surgical clip 1114*a* to its tissue-ready state, the jaw members 1104, 1106 may be actuated and otherwise collapsed toward each other. In some embodiments, this may be accomplished through the use of a cam (e.g., the cam 1202 of FIGS. 12A-12C; see also FIGS. 14A-14C) that is slidably engageable with the jaw members 1104, 1106 and, more particularly, with corresponding cam tracks 1310 provided by the jaw members 1104, 1106. As the cam is advanced distally relative to the jaw members 1104, 1106, the cam engages the cam tracks 1310 and correspondingly pushes (collapses) the jaw members 1104, 1106 toward one another.

Figure 13C:
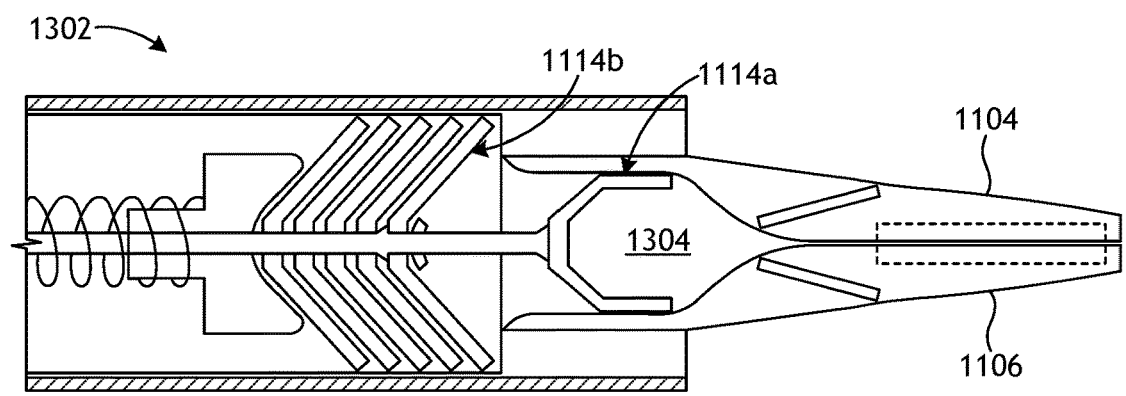

In FIG. 13C, the jaw members 1104, 1106 are depicted as having collapsed or closed toward one another. As the jaw members 1104, 1106 close, the distal-most surgical clip 1114*a* is partially crimped within the pre-forming region 1304 and otherwise plastically or elastically transitioned from the wide state to the tissue-ready state. The jaw members 1104, 1106 may then be re-opened to receive the distal-most surgical clip 1114*a* in its tissue-ready state. Accordingly, as illustrated, when the jaw members 1104, 1106 are actuated for the first time, the pre-forming region 1304 provides a cavity or space that deforms the distal-most surgical clip 1114*a* into its tissue-ready state.

Figure 13D:
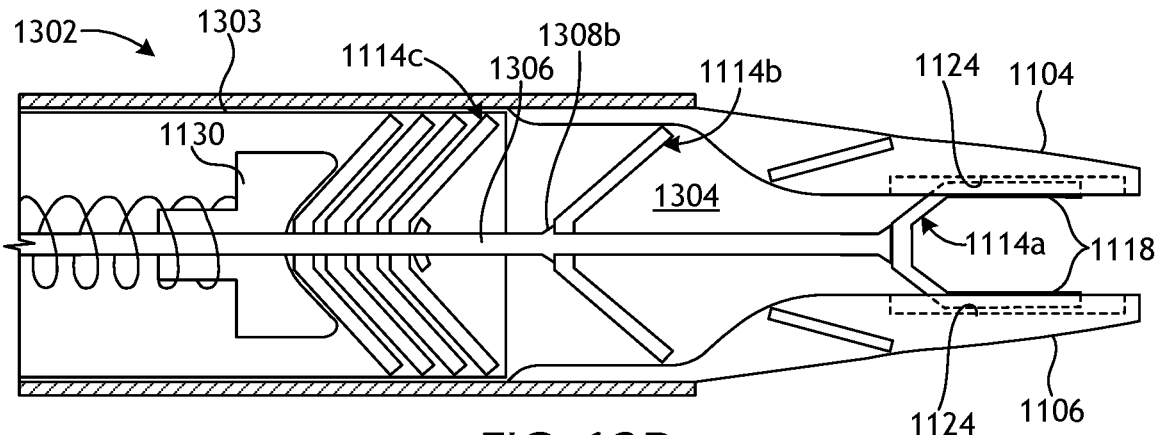

In FIG. 13D, the distal-most surgical clip 1114*a* is shown as having traversed the pre-forming region 1304 and received by the jaw members 1104, 1106 as the feedbar 1306 advances distally. In embodiments including the grooves 1124 defined on each jaw member 1104, 1106, the legs 1118 of the distal-most surgical clip 1114*a* may spring outward and seat themselves within the grooves 1124, which helps retain the distal-most surgical clip 1114*a* in place.

As the feedbar 1306 conveys the distal-most surgical clip 1114*a* into the jaw members 1104, 1106, the penultimate surgical clip 1114*b* may also be simultaneously conveyed into the pre-forming region 1304 as engaged by the second engagement member 1308*b*. More specifically, the penultimate surgical clip 1114*b* may be advanced distally by advancing the feedbar 1306 and providing an axial load on the penultimate surgical clip 1114*b* at the second engagement member 1308*b*. The axial load transferred to the penultimate surgical clip 1114*b* may overcome the spring force of the retention member 1128 to move the penultimate surgical clip 1114*b* distally and into the pre-forming region 1304. In other embodiments, however, the retention member 1128 may be actuated or otherwise moved to allow the feedbar 1306 to distally move the penultimate surgical clip 1114*b*.

After the penultimate surgical clip 1114*b* bypasses the retention member 1128, the feeder shoe 1130 may operate to advance the remaining surgical clips 1114 distally within the clip track 1303 until an antepenultimate surgical clip 1114*c* is received and retained by the retention member 1128.

The penultimate surgical clip 1114*b* is received into the pre-forming region 1304 in its wide state, and may be transitioned to its tissue-ready state in the same process described above to transition the distal-most surgical clip 1114*a* to the tissue-ready state. Collapsing or closing the jaw members 1104, 1106 a second time, however, will also crimp the distal-most surgical clip 1114*a* received between the jaw members 1104, 1106.

Figure 13E:
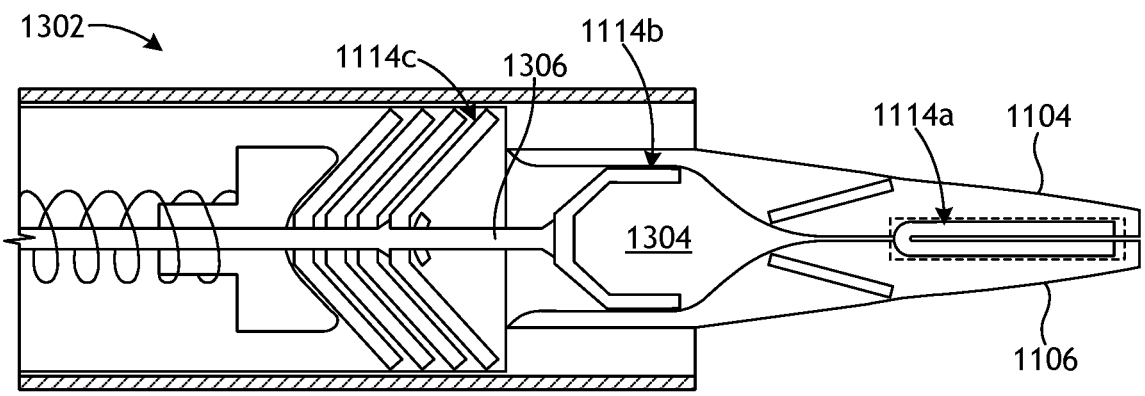

In FIG. 13E, the jaw members 1104, 1106 are depicted as having collapsed or closed toward one another a second time. As the jaw members 1104, 1106 close for the second time, the distal-most surgical clip 1114*a* is crimped between the jaw members 1104, 1106 and the penultimate surgical clip 1114*b* is simultaneously partially crimped within the pre-forming region 1304 and otherwise transitioned from the wide state to the tissue-ready state. At this point, the jaw members 1104, 1106 may then be re-opened and the penultimate surgical clip 1114*b* may be advanced distally to be received by the jaw members 1104, 1106. Prior to closing the jaw members 1104, 1106 the second time, the feedbar 1306 may be retracted to engage the first engagement member 1308*a* on the penultimate surgical clip 1114*b*, and the second engagement member 1308*b* may be engaged with the antepenultimate surgical clip 1114*c*.

Accordingly, to operate the end effector 1302, a user may be required to "prime" the device by advancing surgical clips 1114 twice prior to being able to crimp the distal-most surgical clip 1114*a* between the jaw members 1104, 1106. Once properly primed, however, the end effector 1302 will function by crimping the distal-most surgical clip 1114*a* each time the device is fired, and the penultimate and antepenultimate surgical clips 1114b,c are automatically advanced and fed through the same process.

Figure 14A:
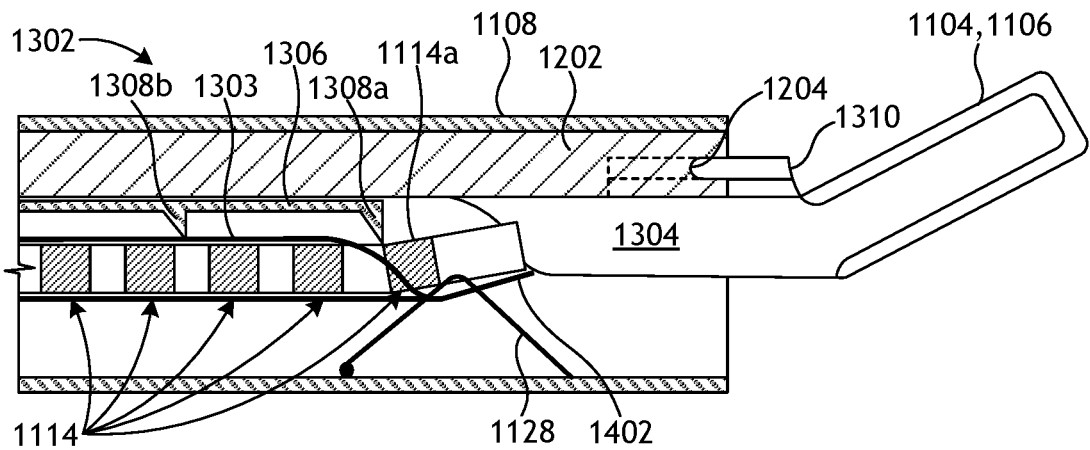
FIGS. 14A-14C are partial cross-sectional side views of the end effector of FIGS. 13A-13E.
Figure 14B:
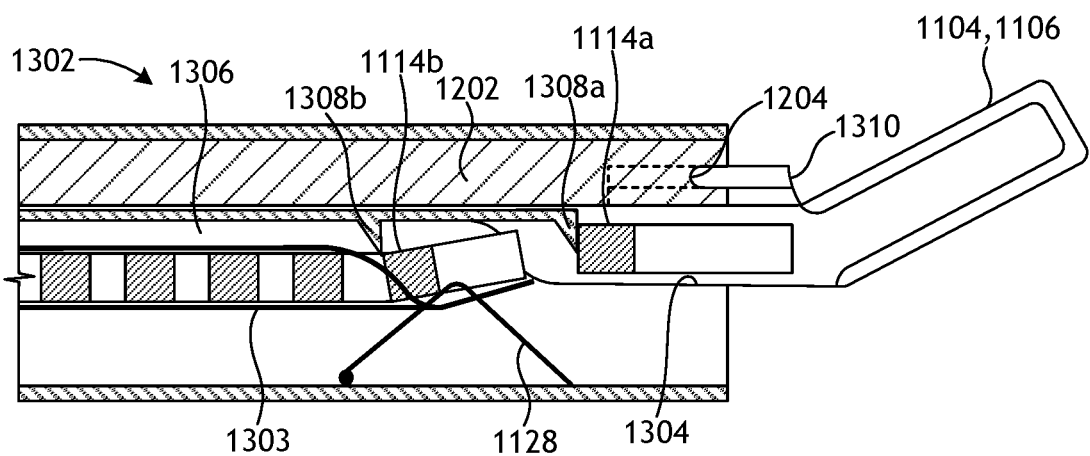
Figure 14C:
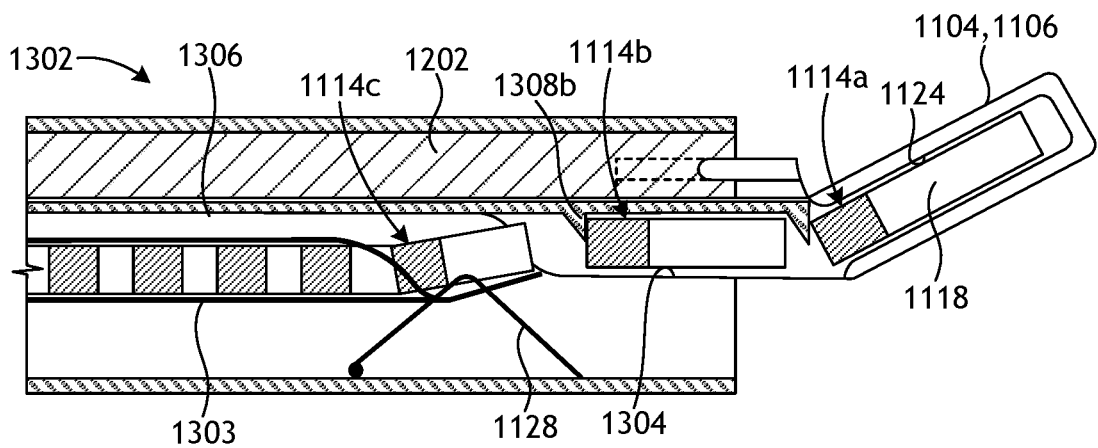

FIGS. 14A-14C are partial cross-sectional side views of the end effector 1302 of FIGS. 13A-13E. Similar to FIGS. 13A-13E, FIGS. 14A-14C provide progressive views of the end effector 1302 during example operation of feeding the surgical clips 1114 into the jaw members 1104, 1106 for forming and crimping in the two-stage process.

Referring first to FIG. 14A, the end effector 1302 may further include the cam 1202 that is slidably engageable with the jaw members 1104, 1106. Again, the cam 1202 may be arranged within the body 1108, but can alternatively be arranged external to the body 1108, and the distal end of the cam 1202 includes the tapering recess or camming channel 1204 formed therein for slidably receiving the corresponding cam tracks 1310 provided by the jaw members 1104, 1106. As the cam 1202 is actuated and advanced distally, the camming channel 1204 slidably engages the cam tracks 1310 and thereby pushes (collapses) the jaw members 1104, 1106 toward one another and toward a closed position.

As illustrated, the surgical clips 1114 are shown arranged within the clip track 1303 and at least partially nested within each other, as described above. Moreover, the retention member 1128 is depicted as engaging the distal-most surgical clip 1114a to prevent the stacked surgical clips 1114 from further advancing distally. In the illustrated embodiment, the retention member 1128 is depicted as a passive gate spring that engages the distal-most surgical clip 1114a. The retention member 1128 exhibits a spring force sufficient to retain the stacked surgical clips 1114 in place until the distal-most surgical clip 1114a is acted upon by the feedbar 1306.

In some embodiments, the distal end of the clip track 1303 may provide or otherwise define a ramped portion 1402. The ramped portion 1402 may be configured to reposition (elevate) the surgical clips 1114 to enable the first and second engagement members 1308a,b of the feedbar 1306 to engage and distally advance the surgical clips 1114 positioned on the ramped portion 1402. The retention member 1128 may extend through the ramped portion 1402 to retain the surgical clip 1114 positioned thereon and thereby retain the remaining surgical clips 1114 within the clip track 1303.

To advance the distal-most surgical clip 1114a distally, the feedbar 1306 may be advanced until the first engagement member 1308a engages the distal-most surgical clip 1114a, which is positioned on the ramped portion 1402. In the illustrated embodiment, the feedbar 1306 applies an axial load that urges the distal-most surgical clip 1114a against the retention member 1128, which flexes downward and out of the way, and thereby allows the distal-most surgical clip 1114a to exit the clip track 1303 and enter the pre-forming region 1304.

In FIG. 14B, the distal-most surgical clip 1114a is shown being advanced distally by the feedbar 1306 and into the pre-forming region 1304. Once the distal-most surgical clip 1114a bypasses the retention member 1128, the feeder shoe 1130 (FIGS. 13A-13E) distally advances the remaining surgical clips 1114 positioned within the clip track 1303 until the penultimate surgical clip 1114b is received and retained by the retention member 1128. In at least one embodiment, advancing the distal-most surgical clip 1114a into the pre-forming region 1304 may also advance the second engagement member 1308b of the feedbar 1306 into engagement with the penultimate surgical clip 1114b. In other embodiments, however, the second engagement member 1308b does not engage the penultimate surgical clip 1114b when the distal-most surgical clip 1114a is advanced into the pre-forming region 1304.

While in the pre-forming region 1304, the distal-most surgical clip 1114a may be transitioned from its wide state to its tissue-ready state. As discussed above, this may be accomplished by actuating the cam 1202 to collapse or close the jaw members 1104, 1106. As the cam 1202 is advanced distally relative to the jaw members 1104, 1106, the camming channel 1204 engages the cam tracks 1310 and correspondingly pushes (collapses) the jaw members 1104, 1106 toward one another. As the jaw members 1104, 1106 close, the distal-most surgical clip 1114a is partially crimped within the pre-forming region 1304 and otherwise plastically or elastically transitioned from the wide state to the tissue-ready state. The jaw members 1104, 1106 may then be re-opened to receive the tissue-ready distal-most surgical clip 1114a.

In FIG. 14C, the distal-most surgical clip 1114a is shown as having traversed the pre-forming region 1304 and advanced into the jaw members 1104, 1106. In embodiments including the grooves 1124 defined on each jaw member 1104, 1106, the legs 1118 may spring outward and seat themselves within the grooves 1124.

As the feedbar 1306 conveys the distal-most surgical clip 1114a into the jaw members 1104, 1106, the penultimate surgical clip 1114b is simultaneously conveyed into the pre-forming region 1304 as engaged by the second engagement member 1308b. Applying an axial load on the penultimate surgical clip 1114b at the second engagement member 1308b may overcome the spring force of the retention member 1128 to move the penultimate surgical clip 1114b distally and into the pre-forming region 1304.

After the penultimate surgical clip 1114b bypasses the retention member 1128, the feeder shoe 1130 (FIGS. 13A-13E) may again operate to advance the remaining surgical clips 1114 distally within the clip track 1303 until an antepenultimate surgical clip 1114c is received and retained by the retention member 1128.

The penultimate surgical clip 1114b is received into the pre-forming region 1304 in its wide state, and may be transitioned to its tissue-ready state in the same process described above to transition the distal-most surgical clip 1114a to the tissue-ready state. More particularly, the jaw members 1104, 1106 may once again be closed through operation of the cam 1202, which partially crimps the penultimate surgical clip 1114b within the pre-forming region 1304 and transitions the penultimate surgical clip 1114b from the wide state to the tissue-ready state.

Collapsing or closing the jaw members 1104, 1106 the second time, however, will also crimp the distal-most surgical clip 1114a received between the jaw members 1104, 1106. At this point, the jaw members 1104, 1106 may then be re-opened and the penultimate surgical clip 1114b may be advanced distally to be received by the jaw members 1104, 1106. Prior to closing the jaw members 1104, 1106 the second time, the feedbar 1306 may be retracted to engage the first engagement member 1308a on the penultimate surgical clip 1114b, and the second engagement member 1308b may be engaged with the antepenultimate surgical clip 1114c.

The foregoing operational cycle may be repeated to continue to simultaneously pre-form and crimp surgical clips 1114 until the supply of surgical clips 1114 is exhausted.

Figure 15A:
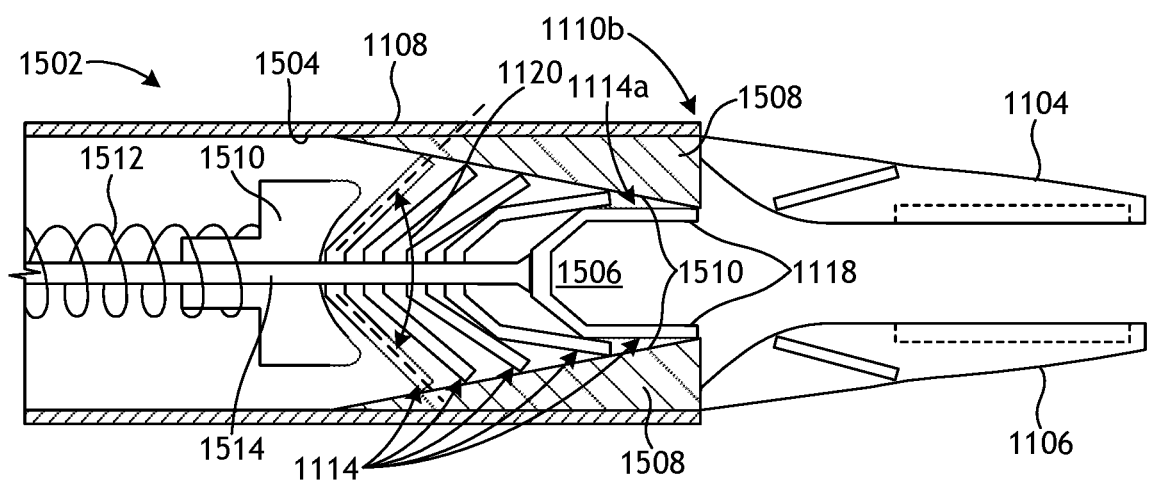
FIGS. 15A and 15B are partial cross-sectional top views of a distal portion of another example end effector.
Figure 15B:
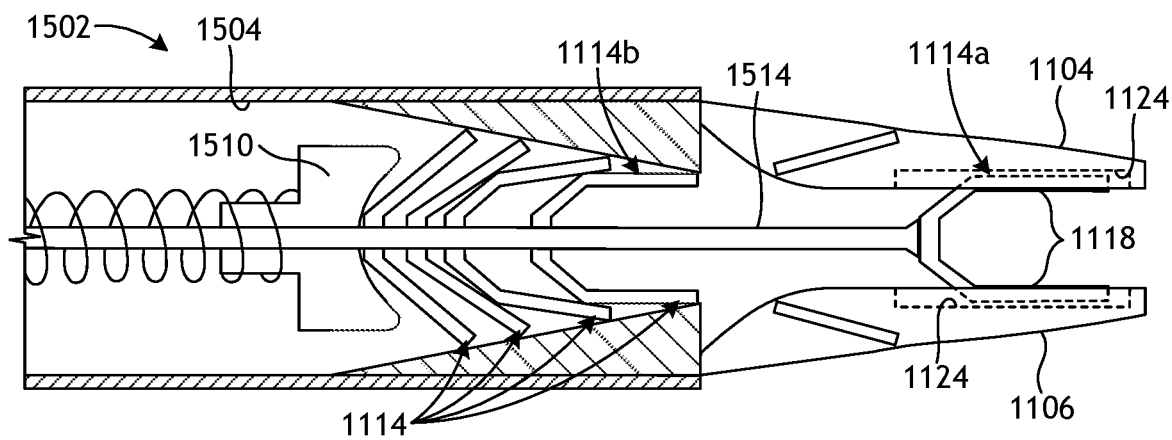

FIGS. 15A and 15B are partial cross-sectional top views of a distal portion of another example end effector 1502, according to one or more embodiments of the present disclosure. The end effector 1502 may be similar in some respects to the end effectors 1102 and 1302 of FIGS. 11A-11C and 13A-13D, respectively, and therefore may be best understood with reference thereto, where like numerals will correspond to like components not described again in detail. FIGS. 15A and 15B illustrate progressive views of the end effector 1502 during example operation of feeding surgical clips 1114 into the jaw members 1104, 1106 for crimping.

Referring first to FIG. 15A, the end effector 1502 includes the elongate body 1108 and the jaw members 1104, 1106 extend out of or otherwise protrude from the distal end 1110b of the body 1108. The end effector 1502 further includes a clip track 1504 configured to contain and otherwise house the surgical clips 1114. In some embodiments, the body 1108 defines or otherwise provides the clip track 1504. In other embodiments, however, the clip track 1504 may comprise a separate structural component that is removably positioned within the body 1108. Similar to the prior embodiments, the surgical clips 1114 may exhibit the diverging opening angle 1120, which allows the surgical clips 1114 to be arranged within the clip track 1504 in a generally nested relationship. While five surgical clips 1114 are depicted in FIG. 15A, more or less than five may be employed, without departing from the scope of the disclosure.

The end effector 1502 may further include a pre-forming region 1506 configured to receive and progressively transition the surgical clips 1114 from the wide state to the tissue-ready state. In some embodiments, the pre-forming region 1506 is defined by the body 1108, but may alternatively be provided by the clip track 1504. In yet other embodiments, the pre-forming region 1506 may comprise a separate structural component that is removably positioned within the body 1108. As illustrated, the pre-forming region 1506 may comprise opposed ramped (angled) surfaces 1508 configured to successively reduce (minimize) the diverging opening angle 1120 of the surgical clips 1114 as they are advanced distally toward the jaw members 1104, 1106. The surgical clips 1114 may be plastically or elastically deformed as they traverse the pre-forming region 1506 in the distal direction.

The end effector 1502 further includes a feeder shoe 1510 configured to apply an axial load in the distal direction on the surgical clips 1114 positioned within the clip track 1504. The axial load forces the surgical clips 1114 through the pre-forming region 1506 to transition the surgical clips 1114 from wide to tissue-ready states. In some embodiments, as illustrated, the feeder shoe 1510 may include a compression spring 1512 that engages a proximal end of the feeder shoe 1510 to provide a passive and constant axial load on the surgical clips 1114. The spring force of the compression spring 1512 may be sufficient to force the surgical clips 1114 through the pre-forming region 1506 until the last surgical clip 1114 is progressively and properly transitioned to the tissue-ready state. In other embodiments, however, the feeder shoe 1510 may include or comprise an actuatable device or mechanism that selectively supplies the axial load. In such embodiments, the feeder shoe 1510 may apply the axial load only to advance the surgical clips 1114 a predetermined distance within the clip track 1504, and thereby progressively advance the surgical clips 1114 through the pre-forming region 1506.

A feedbar 1514 may be included and configured to engage and move the distal-most surgical clip 1114a from the pre-forming region 1506 and to the jaw members 1104, 1106. In some embodiments, the feedbar 1514 may extend to the end effector 1502 from a drive housing (e.g., the drive housings 206, 606 of FIGS. 2 and 6, respectively). At the drive housing, the feedbar 1514 may be operatively coupled to an actuating mechanism or device configured to cause longitudinal translation of the feedbar 1514. In one embodiment, for example, the feedbar 1514 may be operatively coupled to and otherwise extend from one or more translatable driven gears, such as the first and second driven gears 504a,b of FIG. 5. In embodiments with an articulable wrist, the feedbar 1514 may be made of a flexible material and extend through the wrist. Alternatively, the feedbar 1514 may be operatively coupled to a cable-driven worm gear arranged distal to the wrist and the associated drive cable(s) that moves the worm gear extend through the wrist.

With additional reference to FIG. 15B, example operation of feeding the surgical clips 1114 into the jaw members 1104, 1106 is now provided. In FIG. 15A, the feeder shoe 1510 is shown urging the stack of surgical clips 1114 in the distal direction and through the pre-forming region 1506. As they traverse the ramped surfaces 1508 of the pre-forming region 1506, the surgical clips 1114 progressively transition from the wide state to the tissue-ready state. More specifically, the legs 1118 of each surgical clip 1114 slidably engage the inner walls of the pre-forming region 1506 as the surgical clips 1114 advance distally. The distally converging and ramped configuration of the ramped surfaces 1508 progressively reduces the diverging opening angle 1120 to produce tissue-ready surgical clips at or near the distal end of the ramped surfaces 1508.

As illustrated in FIG. 15A the distal-most surgical clip 1114a has been transitioned to the tissue-ready state. To advance the distal-most surgical clip 1114a toward the jaw members 1104, 1106, the feedbar 1514 may be advanced distally until engaging the distal-most surgical clip 1114a.

In FIG. 15B, the distal-most surgical clip 1114a is shown as having traversed the pre-forming region 1506 and being advanced by the feedbar 1514 to be received within the jaw members 1104, 1106. In embodiments including the grooves 1124 defined on each jaw member 1104, 1106, the legs 1118 may spring outward and seat themselves within the grooves 1124, which may help retain the surgical clip 1114 in place. Otherwise, the distal-most surgical clip 1114 may be retained between the jaw members 1104, 1106 via an interference. At this point, the jaw members 1104, 1106 may be actuated to collapse or close and thereby crimp the distal-most surgical clip 1114a therebetween.

Once the distal-most surgical clip 1114a is advanced out of the pre-forming region 1506, the feeder shoe 1510 may be configured to distally advance the remaining surgical clips 1114 positioned within the clip track 1504 and further into the pre-forming region 1506. As a result, the penultimate surgical clip 1114b may be fully transitioned from the wide state to the tissue-ready state and ready to be advanced distally to the jaw members 1104, 1106 with the feedbar 1514.

The foregoing operational cycle may be repeated to continue to progressively form tissue-ready surgical clips 1114 and advance the tissue-ready surgical clips 1114 to the jaw members 1104, 1106 to be crimped until the supply of surgical clips 1114 is exhausted.

Embodiments disclosed herein include:

A. An end effector for a surgical clip applier that includes an elongate body, a clip track provided within the body and containing one or more surgical clips, wherein each surgical clip includes a crown and a pair of legs extending longitudinally from the crown and diverging from each other at a diverging opening angle, a pre-forming region provided within the body and arranged to receive and deform the one or more surgical clips from a first state, where the pair of legs diverge at the diverging opening angle, and a second state, where the diverging opening angle is minimized, and first and second jaw members positioned at a distal end of the body and arranged to receive the one or more surgical clips from the pre-forming region in the second state.

B. A method of operating an end effector of a surgical clip applier that includes positioning the end effector adjacent a patient for operation, the end effector including an elongate body, a clip track provided within the body and containing one or more surgical clips, wherein each surgical clip includes a crown and a pair of legs extending longitudinally from the crown and diverging from each other at a diverging opening angle, a pre-forming region provided within the body and arranged to receive the one or more surgical clips from the clip track, and first and second jaw members positioned at a distal end of the body and arranged to receive the one or more surgical clips from the pre-forming region. The method further including advancing a distal-most surgical clip of the one or more surgical clips from the clip track to the pre-forming region, deforming the distal-most surgical clip in the pre-forming region from a first state, where the pair of legs of the distal-most surgical clip diverge at the diverging opening angle, and a second state, where the diverging opening angle is minimized, and advancing the distal-most surgical clip from the pre-forming region to the first and second jaw members in the second state.

C. A surgical clip applier that includes a drive housing, an elongate shaft that extends from the drive housing, and an end effector arranged at a distal end of the elongate shaft. The end effector includes an elongate body, a clip track provided within the body and containing one or more surgical clips, wherein each surgical clip includes a crown and a pair of legs extending longitudinally from the crown and diverging from each other at a diverging opening angle, a pre-forming region provided within the body and arranged to receive and deform the one or more surgical clips from a first state, where the pair of legs diverge at the diverging opening angle, and a second state, where the diverging opening angle is minimized, and first and second jaw members positioned at a distal end of the body and arranged to receive the one or more surgical clips from the pre-forming region in the second state.

Each of embodiments A, B, and C may have one or more of the following additional elements in any combination: Element 1: wherein the one or more surgical clips comprises a plurality of surgical clips arranged in series within the clip track, and wherein more distal surgical clips of the plurality of surgical clips are at least partially nested within more proximal surgical clips of the plurality of surgical clips. Element 2: wherein the pre-forming region comprises opposed structural surfaces that converge toward one another in a distal direction. Element 3: wherein the pre-forming region is defined by the first and second jaw members. Element 4: wherein the first and second jaw members are actuated a first time to deform a given surgical clip of the one or more surgical clips from the first state to the second state, and actuated a second time to crimp the given surgical clip between the first and second jaw members. Element 5: further comprising a feeder shoe that applies an axial load on the one or more surgical clips positioned within the clip track to promote sequential feeding of the one or more surgical clips, and a feedbar engageable with a distal-most surgical clip of the one or more surgical clips to convey the distal-most surgical clip to the pre-forming region and subsequently to the first and second jaw members. Element 6: further comprising a retention member that engages one or more surgical clips located distally within the clip track and prevents the one or more surgical clips from advancing into the pre-forming region. Element 7: wherein the retention member comprises a passive biasing device. Element 8: wherein the feeder shoe further comprises a compression spring that supplies the axial load. Element 9: wherein the feedbar advances the distal-most surgical clip through the pre-forming region such that the pair of legs of the distal-most surgical clip slidably engage the inner walls of the pre-forming region to transition the distal-most surgical clip to the second state. Element 10: wherein the feedbar comprises a first engagement member engageable with the distal-most surgical clip, and a second engagement member located proximal to the first engagement member and simultaneously engageable with a penultimate surgical clip of the one or more surgical clips. Element 11: wherein a distal end of the clip track provides a ramped portion that repositions the one or more surgical clips positioned at the ramped portion such that the feedbar is able to engage and distally advance the one or more surgical clips. Element 12: wherein a distal end of the pre-forming region is aligned with the first and second jaw members.

Element 13: wherein the pre-forming region comprises opposed structural surfaces that converge toward one another in a distal direction, and wherein advancing the distal-most surgical clip to the pre-forming region comprises engaging the distal-most surgical clip with a feedbar, conveying the distal-most surgical clip to the pre-forming region with the feedbar, and advancing the distal-most surgical clip through the pre-forming region such that the pair of legs of the distal-most surgical clip slidably engage the opposed structural surfaces of the pre-forming region and transition the distal-most surgical clip to the second state. Element 14: wherein the pre-forming region is defined by the first and second jaw members, and wherein deforming the distal-most surgical clip in the pre-forming region comprises conveying the distal-most surgical clip to the pre-forming region with a feedbar, and actuating the first and second jaw members a first time to deform the distal-most surgical clip to the second state within the pre-forming region. Element 15: wherein the feedbar comprises a first engagement member engageable with the distal-most surgical clip, and a second engagement member located proximal to the first engagement member, and wherein advancing the distal-most surgical clip to the first and second jaw members in the second state further comprises advancing the distal-most surgical clip to the first and second jaw members with the feedbar and simultaneously engaging the second engagement member on a penultimate surgical clip of the one or more surgical clips and advancing the penultimate surgical clip to the pre-forming region, and actuating the first and second jaw members a second time to crimp the distal-most surgical clip and simultaneously deform the penultimate surgical clip to the second state within the pre-forming region.

Element 16: further comprising an articulable wrist joint interposing the end effector and the elongate shaft.

By way of non-limiting example, exemplary combinations applicable to A, B, and C include: Element 3 with Element 4; Element 5 with Element 6; Element 6 with Element 7; Element 5 with Element 8; Element 5 with Element 9; Element 5 with Element 10; Element 5 with Element 11; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
   an elongate body; first and second jaw members positioned at a distal end of the body;
   a clip track provided within the body;
   one or more surgical clips contained within the clip track, wherein each surgical clip includes a crown and a pair of legs extending longitudinally from the crown and diverging from each other at a diverging opening angle;
   a pre-forming region defined by the clip track and comprising opposed structural surfaces that converge toward one another in a distal direction; and
   a feedbar engageable with a distal-most surgical clip of the one or more surgical clips to advance the distal-most surgical clip through the pre-forming region and thereby transition the distal-most surgical clip from a first state, where the pair of legs diverge at the diverging opening angle, to a second state, where the diverging opening angle is minimized;
   and the distal-most surgical clip is prepared to be received by the first and second jaw members and crimped.

2. The end effector of claim 1, wherein the one or more surgical clips comprises a plurality of surgical clips arranged in series within the clip track, and wherein more distal surgical clips of the plurality of surgical clips are at least partially nested within more proximal surgical clips of the plurality of surgical clips.

3. The end effector of claim 1, further comprising
   a feeder shoe that applies an axial load on the one or more surgical clips positioned within the clip track to promote sequential feeding of the one or more surgical clips;
   wherein the feedbar conveys the distal-most surgical clip to the first and second jaw members.

4. The end effector of claim 3, further comprising a retention member that engages the one or more surgical clips located distally within the clip track and prevents the one or more surgical clips from advancing into the pre-forming region.

5. The end effector of claim 4, wherein the retention member comprises a passive biasing device.

6. The end effector of claim 3, wherein the feeder shoe further comprises a compression spring that supplies the axial load.

7. The end effector of claim 3, wherein the feedbar advances the distal-most surgical clip through the pre-forming region such that the pair of legs of the distal-most surgical clip slidably engage the inner walls of the pre-forming region to transition the distal-most surgical clip to the second state.

8. The end effector of claim 3, wherein a distal end of the clip track provides a ramped portion that repositions the one or more surgical clips positioned at the ramped portion such that the feedbar is able to engage and distally advance the one or more surgical clips.

9. The end effector of claim 1, wherein a distal end of the pre-forming region is aligned with the first and second jaw members.

10. The end effector of claim 1, wherein the one or more surgical clips comprise a proximal surgical clip and a distal surgical clip, and wherein, when the proximal and distal surgical clips are contained within the clip track, the pair of legs of the proximal surgical clip extends past and partially overlaps the pair of legs of the distal surgical clip.

11. A method of operating an end effector of a surgical clip applier, comprising:
   positioning the end effector adjacent a patient for operation, the end effector including:
      an elongate body; first and second jaw members positioned at a distal end of the body;
      a clip track provided within the body;
      one or more surgical clips contained within the clip track, wherein each surgical clip includes a crown and a pair of legs extending longitudinally from the crown and diverging from each other at a diverging opening angle;
      a pre-forming region defined by the clip track and comprising opposed structural surfaces that converge toward one another in a distal direction;
   distally advancing a distal-most surgical clip of the one or more surgical clips through the pre-forming region with a feedbar;
   deforming the distal-most surgical clip in the pre-forming region from a first state, where the pair of legs of the distal-most surgical clip diverge at the diverging opening angle, to a second state, where the diverging opening angle is minimized and the distal-most surgical clip is prepared to be received by the first and second jaw members and crimped; and advancing the distal-most surgical clip from the pre-forming region to the first and second jaw members in the second state with the feed bar.

12. The method of claim 11, wherein distally advancing the distal-most surgical clip through the pre-forming region comprises advancing the distal-most surgical clip through the pre-forming region such that the pair of legs of the distal-most surgical clip slidably engage the opposed structural surfaces of the pre-forming region and transition the distal-most surgical clip to the second state.

13. A surgical clip applier, comprising:

a drive housing;

an elongate shaft that extends from the drive housing; and an end effector arranged at a distal end of the elongate shaft, the end effector including:

an elongate body; first and second jaw members positioned at a distal end of the body;

a clip track provided within the body;

one or more surgical clips contained within the clip track, wherein each surgical clip includes a crown and a pair of legs extending longitudinally from the crown and diverging from each other at a diverging opening angle;

a pre-forming region defined by the clip track and comprising opposed structural surfaces that converge toward one another in a distal direction; and a feedbar engageable with a distal-most surgical clip of the one or more surgical clips to advance the distal-most surgical clip through the pre-forming region and thereby transition the distal-most surgical clip from a first state, where the pair of legs diverge at the diverging opening angle, to a second state, where the diverging opening angle is minimized and the distal-most surgical clip is prepared to be received by the first and second jaw members and crimped.

14. The surgical clip applier of claim 13, further comprising an articulable wrist joint interposing the end effector and the elongate shaft.

15. The surgical clip applier of claim 13, wherein the one or more surgical clips comprise a proximal surgical clip and a distal surgical clip, and wherein, when the proximal and distal surgical clips are contained within the clip track, the pair of legs of the proximal surgical clip extends past and partially overlaps the pair of legs of the distal surgical clip.

* * * * *